US007566804B2

(12) United States Patent
Diefenbacher et al.

(10) Patent No.: US 7,566,804 B2
(45) Date of Patent: Jul. 28, 2009

(54) PROCESS FOR PREPARING ACRYLIC ACID

(75) Inventors: Armin Diefenbacher, Freisbach (DE); Ulrich Hammon, Mannheim (DE); Volker Schliephake, Schifferstadt (DE); Georg Sieder, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/020,264

(22) Filed: Jan. 25, 2008

(65) Prior Publication Data

US 2008/0183014 A1    Jul. 31, 2008

Related U.S. Application Data

(60) Provisional application No. 60/988,619, filed on Nov. 16, 2007, provisional application No. 60/886,771, filed on Jan. 26, 2007.

(30) Foreign Application Priority Data

Jan. 26, 2007  (DE)  .................. 10 2007 004 960
Nov. 16, 2007  (DE)  .................. 10 2007 055 086

(51) Int. Cl.
*C07C 51/42* (2006.01)
*C07C 51/16* (2006.01)

(52) U.S. Cl. ...................... 562/600; 562/532
(58) Field of Classification Search .............. None
See application file for complete search history.

(56) References Cited

U.S. PATENT DOCUMENTS

| 6,498,272 | B1 * | 12/2002 | Schroder et al. ............ 562/600 |
| 6,679,939 | B1 | 1/2004 | Thiel et al. |
| 6,939,991 | B2 | 9/2005 | Thiel et al. |
| 7,112,695 | B2 | 9/2006 | Eck et al. |
| 7,118,098 | B2 | 10/2006 | Thiel et al. |
| 7,393,436 | B2 | 7/2008 | Eck et al. |
| 2004/0256319 | A1 | 12/2004 | Hammon et al. |
| 2005/0006299 | A1 | 1/2005 | Heilek et al. |
| 2006/0004229 | A1 * | 1/2006 | Dieterle et al. ............ 562/527 |
| 2008/0183013 | A1 | 7/2008 | Dubois et al. |

FOREIGN PATENT DOCUMENTS

| DE | 199 24 532 A 1 | 11/2000 |
| DE | 199 24 533 A1 | 11/2000 |
| DE | 101 56 016 A1 | 6/2003 |
| DE | 102 35 847 A1 | 8/2003 |
| DE | 102 23 058 A1 | 12/2003 |
| DE | 102 43 625 A1 | 4/2004 |
| DE | 103 32 758 A1 | 5/2004 |
| EP | 1 710 227 A1 | 10/2006 |
| WO | WO 00/53560 | 9/2000 |
| WO | WO 01/77056 A1 | 10/2001 |
| WO | WO 03/095411 A1 | 11/2003 |
| WO | WO 2004/035514 A1 | 4/2004 |
| WO | WO 2006/092272 A2 | 9/2006 |
| WO | WO 2006/114506 | 11/2006 |

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

A process for preparing acrylic acid, in which an acrylic acid-comprising product gas mixture obtained by catalytic gas phase partial oxidation of a $C_3$ precursor of acrylic acid is fractionally condensed in a condensation column provided with internals ascending into itself with side draw removal of crude acrylic acid and with liquid phase draw removal of acrylic acid-comprising acid water, and acrylic acid present in acid water is taken up into an extractant and then removed from the extractant and recycled into the condensation column, or taken up in aqueous metal hydroxide, or sent to further purification of the crude acrylic acid.

25 Claims, No Drawings

PROCESS FOR PREPARING ACRYLIC ACID

DESCRIPTION

The invention relates to a process for preparing acrylic acid, in which a product gas mixture comprising acrylic acid, steam and secondary components is obtained by heterogeneously catalyzed gas phase partial oxidation of at least one $C_3$ precursor of acrylic acid with molecular oxygen over solid-state catalysts at elevated temperature, the temperature of the product gas mixture comprising acrylic acid, steam and secondary components is, if appropriate, reduced by direct and/or indirect cooling, and the product gas mixture comprising acrylic acid, steam and secondary components is then passed into a condensation column equipped with separating internals, allowed to ascend into itself within the condensation column and thus fractionally condensed, and crude acrylic acid comprising water and secondary components depleted overall is conducted as the target product out of the condensation column via a first side draw disposed above the feed point of the product gas mixture into the condensation column, as are acid water still comprising acrylic acid and secondary components via a second liquid phase draw (preferably a side draw) disposed above the first side draw and a residual gas mixture comprising secondary components having lower boiling points (boiling at lower temperature (based on atmospheric pressure)) than water at the top of the condensation column and a bottoms liquid still comprising acrylic acid and conversion products and secondary components having higher boiling points (based on atmospheric pressure) than acrylic acid from the bottom space of the condensation column, a portion of the acid water withdrawn is recycled as such and/or after cooling thereof as reflux liquid into the condensation column and the crude acrylic acid is subjected if appropriate to at least one further thermal separation process for the purpose of its further purification.

Acrylic acid is an important intermediate which finds use, for example, in the preparation of polymer dispersions (if appropriate also in the form of its esters with alkanols) and of water-superabsorbing polymers.

Acrylic acid is obtainable, inter alia, by heterogeneously catalyzed gas phase partial oxidation of $C_3$ precursors (of $C_3$ precursor compounds) of acrylic acid (this term shall in particular encompass those chemical compounds which are obtainable in a formal sense by reduction of acrylic acid; known $C_3$ precursors of acrylic acid are, for example, propane, propene, acrolein, propionaldehyde and propionic acid; the term shall also comprise precursor compounds of the aforementioned compounds, for example glycerol (proceeding from glycerol, acrylic acid can be obtained, for example, by heterogeneously catalyzed oxidative dehydration in the gas phase; cf., for example, EP-A 1 710 227, WO 06/114506 and WO 06/092272)) with molecular oxygen over solid-state catalysts at elevated temperature.

In this preparation, the starting gases mentioned, generally diluted with inert gases, for example nitrogen, $CO_2$, saturated hydrocarbons and/or steam, are passed in a mixture with molecular oxygen at elevated temperatures and, if appropriate, elevated pressure over (for example transition metal) mixed oxide catalysts and converted oxidatively to a product gas mixture which comprises acrylic acid, water and undesired by-products, for example furfurals, benzaldehyde, acetone, formaldehyde and maleic anhydride, etc., from which the acrylic acid has to be removed (the by-products and the inert diluent gases other than steam shall be encompassed in this document under the term "secondary components"; this term shall also comprise the polymerization inhibitors typically added in the acrylic acid removal processes).

Proceeding from propionaldehyde and/or propionic acid, the heterogeneously catalyzed gas phase partial oxidation with molecular oxygen is at least partly an oxidative dehydrogenation.

As described at the outset, the documents DE-A 199 24 533, DE-A 199 24 532, WO 01/77056, DE-A 101 56 016, DE-A 102 43 625, DE-A 102 23 058, DE-A 102 35 847, WO 2004/035514, WO 00/53560 and DE-A 103 32 758 disclose processes for preparing acrylic acid in which a basic removal of crude acrylic acid is undertaken by fractional condensation of the product gas mixture of the heterogeneously catalyzed gas phase partial oxidation. The term "crude acrylic acid" expresses that the acrylic acid withdrawn via the first side draw is not a pure product but rather a mixture which, as well as acrylic acid (generally ≧50 or ≧60% by weight, usually ≧70 or ≧80% by weight, in many cases ≧90% by weight and frequently ≧95% by weight or more of the total weight), also comprises water and secondary components, for example lower aldehydes (e.g. furfurals, acrolein, benzaldehyde), lower carboxylic acids (e.g. acetic acid, propionic acid, formic acid), etc. In each case, the total content of water and secondary components, based on the content of acrylic acid, is lower in the crude acrylic acid than in the product gas mixture of the gas phase partial oxidation, which is why it is also said that the crude acrylic acid comprises these constituents in depleted form overall (individual constituents may, in contrast, be present in the crude acrylic acid in comparatively enriched form).

In some cases, the purity of the crude acrylic acid thus removed is already sufficient for the contemplated end use of the acrylic acid (for example for the purpose of esterification thereof, or for the purpose of forming polymers obtainable by free-radical polymerization). In many cases, the crude acrylic acid removed will, however, be subjected to at least one further thermal separation process in order to obtain, from the crude acrylic acid, a purer acrylic acid (having a higher acrylic acid content in % by weight compared to the crude acrylic acid), which has the degree of purity required for the particular end use.

Thermal separation processes are understood to mean those in which, with supply or withdrawal of (generally thermal) energy, a physically at least biphasic system is obtained, there being heat and mass transfer owing to the temperature and quantitative gradients existing between the phases, which ultimately causes the desired separation, and extraction.

Frequently, thermal separation processes are performed in separating columns comprising separating internals, in which the aforementioned at least two phases are conducted generally in countercurrent to one another. In many cases, one of the two phases is gaseous (it is generally conducted as an ascending phase in a separating column) and the other liquid (it is generally conducted as a descending phase in a separating column). In principle, the at least two phases may, though, also be liquid (for example in the case of an extraction) or solid and liquid (for example in the case of a crystallization) or solid and gaseous (for example in the case of an adsorption).

Examples of configurations of thermal separation processes in which one of the at least two phases is liquid and one is gaseous, and hence a natural element of the term "thermal separation process" used in this document, are rectification (an ascending vapor phase is conducted in countercurrent to a descending liquid phase in the separating column) and desorption (the inverse process of absorption; the gas dissolved in a liquid phase is conducted out of the liquid phase by lowering the pressure over the liquid phase, by increasing the temperature of the liquid phase and/or by conducting a gas phase through the liquid phase; when the conduction of a gas phase through is involved, the desorption is also referred to as stripping). However, absorption (generally, a gas ascending in a separating column is conducted in countercurrent to at least one absorbent descending in liquid form in the separating column) and fractional condensation of a gas mixture (gas/liquid phase example) are also part of the term "thermal separation process". A particularly favorable thermal separation process for the further purification of crude acrylic acid is crystallizative further purification (crystallization).

A disadvantage of the known processes for the basic removal of crude acrylic acid by fractional condensation of the product gas mixture of a heterogeneously catalyzed gas phase partial oxidation of at least one $C_3$ precursor of acrylic acid is, however, the additional occurrence of acid water which still comprises acrylic acid and secondary components. The term "acid water" expresses firstly that the acid water comprises generally $\geq 50\%$ by weight, frequently $\geq 60\%$ by weight, in many cases $\geq 70\%$ by weight and often $\geq 80\%$ by weight of water (this is generally both water of reaction and diluent water (steam) used as an inert diluent gas in the course of the gas phase partial oxidation).

However, it also expresses that it also comprises, as well as water, secondary component acids, for example propionic acid, acetic acid and formic acid, and also acrylic acid, and hence has a pH of <7 (the total content of the secondary component carboxylic acids other than acrylic acid is generally, based on the weight of the acid water, $\leq 10\%$ by weight, in some cases $\leq 5\%$ by weight).

Normally, the acrylic acid content of the acid water will be from 4 or 5 to 15% by weight, frequently approx. 10% by weight. A disadvantage of the processes for the basic removal of acrylic acid from the product gas mixture of the heterogeneously catalyzed gas phase partial oxidation recommended in the prior art is that they send the acid water which still comprises acrylic acid and has not been recycled into the rectification column to incineration in its entirety (cf., in particular, DE-A 102 43 625, WO 2004/035514 and DE-A 103 32 758).

This is disadvantageous in that the acid water incineration reduces, for example, the yield of the desired acrylic acid product.

In view of the prior art described, it was an object of the present invention to provide an improved process for preparing acrylic acid, which is notable especially in that it ensures an increased yield of acrylic acid without significantly impairing the purity thereof.

Accordingly, a process has been found for preparing acrylic acid, in which a product gas mixture comprising acrylic acid, steam and secondary components is obtained by heterogeneously catalyzed gas phase partial oxidation of at least one $C_3$ precursor (a $C_3$ precursor compound) of acrylic acid with molecular oxygen over solid-state catalysts at elevated temperature, the temperature of the product gas mixture comprising acrylic acid, steam and secondary components is, if appropriate, reduced by direct (by direct contact with a cooling liquid) and/or indirect cooling, and the product gas mixture comprising acrylic acid, steam and secondary components is then passed into a condensation column equipped with separating internals, allowed to ascend into itself within the condensation column and thus fractionally condensed, and crude acrylic acid comprising water and secondary components depleted overall is conducted as the target product out of the condensation column via a first side draw disposed above the feed point of the product gas mixture into the condensation column, as are acid water still comprising acrylic acid and secondary components via a second liquid phase draw (preferably a side draw: all statements in this document apply in particular in the case of such an acid water side draw) disposed above the first side draw and a residual gas mixture comprising secondary components having lower boiling points (boiling at a lower temperature (based on atmospheric pressure)) than water at the top of the condensation column and a bottoms liquid still comprising acrylic acid and conversion products and secondary components having higher boiling points than acrylic acid from the bottom space of the condensation column, a portion of the acid water withdrawn is recycled as such and/or after cooling thereof as reflux liquid into the condensation column and the crude acrylic acid is subjected if appropriate to at least one further thermal separation process for the purpose of its further purification, wherein acrylic acid present at least in a portion of acid water not recycled into the condensation column is taken up from the acid water into an organic solvent by extraction with the organic solvent to form an organic extract comprising acrylic acid, then the acrylic acid is removed from the organic extract using at least one thermal separation process and acrylic acid removed from the extract is recycled into the condensation column or sent to the further purification of the crude acrylic acid and/or taken up into the aqueous solution of a metal hydroxide.

Advantageously in accordance with the invention, at least 25% by weight, better at least 50% by weight, even better at least 75% by weight and preferably the entirety of the acid water not recycled into the condensation column is extracted and treated further in accordance with the invention.

In principle, all extraction apparatus known for liquid-liquid extractions is useful for the performance of the extraction required in accordance with the invention. This apparatus should as far as possible ensure that a large phase interface area and a fine distribution of these droplets in the continuous phase is obtained, and also rapid and substantially complete phase separation on completion of mass transfer.

In the simplest case, the extraction unit used may be a mixer (for example a stirred vessel or a static mixer) with separator (for example a settling vessel). The stirrers used may in principle be all common stirrers. Examples include disk stirrers, impeller stirrers, crossbeam stirrers, grid stirrers, blade stirrers, anchor stirrers, paddle stirrers, propeller stirrers, helical stirrers and multilevel momentum countercurrent stirrers. The stirrers may also be multistage, i.e. a plurality of stirrers are arranged one on top of another on a common axis. Preference is given to using a two-stage impeller stirrer. Useful settling vessels are in principle all common vessels. Preference is given to using a horizontal vessel. Such an extraction unit can be operated continuously or batchwise, the settling vessel being dispensable in batchwise operation and the phase separation being performed in the stirred vessel. The transition of the substance to be extracted (the material of value) into the absorber phase is effected in the mixer, the separation of the two phases (by virtue of gravity) in the separator. In continuous operation, the separation of the feed into a heavy and light phase in the settling vessel can be improved by internals transverse to the flow direction. Useful internals include in principle all common internals, for example perforated sheets, plates, structured packings and/or random packings. Among the random packings, preference is given to those comprising rings, helices, saddles, Raschig, Intos or Pall rings, barrel or Intalox saddles, Top-Pak, etc., or braids. Particular preference is given to perforated sheets in combination with random packings. The residence time in the settling vessel is typically from 0.05 to 2 h.

When a plurality of mixer-settler units are connected in series, reference is made to a cascade. The units may be connected either in cocurrent or in countercurrent or crosscurrent.

Appropriately from an application point of view, the extraction to be performed in accordance with the invention will be undertaken in an extraction column comprising separating internals. The phase of higher specific gravity enters the column at the top and the phase of lower specific gravity at the bottom. In the column, the two phases move in countercurrent. In principle, extraction columns are equivalent to columns for countercurrent distillation (rectification). In other words, extraction columns suitable for the inventive extraction process may be of a design known per se and have the customary internals.

Possible column types include extraction columns both with and without energy input. Extraction columns which comprise internals in the form of structured packings and/or random packings may be operated either with or without energy input. Among the random packings, preference is given to those comprising rings, helices, saddles, Raschig, Intos or Pall rings, barrel or Intalox saddles, Top-Pak, etc. Structured packings particularly suitable for extraction columns to be used in accordance with the invention are, for example, structured packings from Julius Montz GmbH in D-40705 Hilden, for example the Montz-Pak B1-350 structured packing. Preference is given to using punched structured packings composed of stainless steel sheets. Packed columns with structured packings are known per se to those skilled in the art and are described, for example, in Chem. Ing. Tech. 58 (1986) 1, p. 19-31 and in the Technischen Rundschau Sulzer [Sulzer Technical Review] February 1979, p. 49 ff. from Gebrüder Sulzer Aktiengesellschaft in Winterthur, Switzerland. In addition, extraction columns with internals in the form of trays are also suitable, and a distinction has to be drawn here between pulsed sieve tray columns and crossflow sieve tray columns. In the pulsed sieve tray columns, the two phases are conducted through the passage orifices (generally holes, i.e. circular passage orifices) in the sieve tray. In the upward stroke of the pulsation, the lighter phase is forced upward through the holes of the sieve tray, and the heavy phase correspondingly downward in the downward stroke. The Karr column also works similarly except that it is not the liquid that is pulsed here but rather the sieve trays are moved up and down. The pulsed sieve tray column is preferred. When crossflow sieve tray columns are used, in contrast, the continuous phase runs downward via downcomers from one tray to the next tray and only the dispersed phase is forced through the holes of the sieve trays owing to the density difference (the terms used in this document for mass transfer trays are in line with those of DE-A 103 32 758).

In general, from 1 to 10 theoretical plates are sufficient for the acid water extraction to be performed in accordance with the invention. A theoretical plate (or theoretical separating stage) shall refer in this document quite generally to that spatial unit of a separating column which comprises separating internals and is used for a thermal separation process which brings about an enrichment corresponding to the thermodynamic equilibrium. In other words, the term "theoretical plate" is applicable both to extraction columns with mass transfer trays and to extraction columns with structured packings and/or random packings.

When an extraction column is used for the process according to the invention, the phase which has the higher specific gravity of the two phases will, appropriately from an application point of view, be introduced into the column at the top by means of distributors, with very uniform distribution over the cross section. The phase of lower specific gravity, appropriately from an application point of view, likewise enters the column at the bottom via a distributor. Accordingly, the lighter phase rises and the heavy phase falls in the column. When the lighter of the two phases is dispersed, i.e. it is present in droplet form, the phase separation takes place in the top of the column; in the reverse case in which the heavy phase is dispersed, the phase separation takes place in the bottom of the column. In both cases, favorable droplet sizes have a diameter (a longitudinal dimension) in the range from 1 to 10 mm, preferably in the range from 2 to 5 mm.

Advantageously in accordance with the invention, the extractant will have a higher boiling point than acrylic acid (based in each case on atmospheric pressure), since this generally facilitates the subsequent removal of the acrylic acid from the organic extract.

In the extraction to be performed in accordance with the invention, the situation will therefore be, with increased probability, that the organic solvent to be used as the extractant has a significantly higher viscosity than water. In this case, it is advantageous in accordance with the invention when the organic extractant which enters the extraction column is present as a dispersed phase and the acid water as a continuous phase (this causes, for example, accelerated mass transfer between the two phases and ultimately enables shorter columns for the same separation result; a continuous aqueous phase also wets extraction columns manufactured from stainless steel and their internals better; furthermore, transport of the substance to be extracted from the continuous phase into the disperse phase leads to a stabilization of the latter (lower coalescence tendency)). When an organic extractant with a higher mass density than the mass density of the acid water is used, this means that the extractant is introduced and dispersed at the top of the column, and the resulting extractant droplets fall downward in the column. In the reverse case, i.e. in the case of use of an extractant with a lower mass density than the mass density of acid water, the extractant is dispersed in the bottom of the column and the resulting extractant droplets ascend in the column. In the types of extraction columns mentioned so far, with internals in the form of structured packings, random packings and/or trays, the undivided continuous phase should efficiently wet the internals selected, since the droplets of the dispersed phase otherwise generally creep along the internals.

In the simplest manner, the organic extractant will be introduced via tubes (which normally have an identical cross section; reference is also made to tube distributors) which have generally round passage orifices (bores), are arranged over the column cross section and extend over the particular cross-sectional length of the normally cylindrical extraction column. When the organic extractant is introduced at the top of the column, the circular passage orifices point downward, and point upward in the case of introduction of the extractant at the bottom of the column. The diameter (the longest dimension) of the aforementioned passage orifices will typically be from 1 mm to 10 mm, preferably from 3 mm to 6 mm and in many cases from 2 to 5 mm. The extractant can be allowed to flow in a simple manner into the distributor tubes and back out of the passage orifices.

In principle, it is also possible to use stirred columns or centrifugal extractors for the acid water extraction to be performed in accordance with the invention. Stirred columns improve the contact of the two phases. All stirrers of the column reside, appropriately from an application point of view, on a common shaft. The column tube is appropriately equipped with stator rings on the walls. The shaft generally arranged in the middle typically has stirrer units such that a stirrer rotates between two stator rings in each case. Examples of stirred columns include the RDC (rotating disk contactor) column, the ARD (asymmetrical rotating disk) column, the Kühni column (stirred column according to Kühni design) or the QVF stirred-cell extractor. Centrifugal extractors utilize centrifugal force for the mixing and separation of the two phases conducted in countercurrent. The centrifugal force also brings about good raffinate/extract separation when the two phases tend to the formation of a stable emulsion. Examples here include the Podbielnak extractor or the Westfalia separator apparatus.

The extraction unit for the process according to the invention is preferably manufactured from the material 1.4571. This also applies to the other apparatus which can be used for the removal of the acrylic acid from the product gas mixture of the heterogeneously catalyzed gas phase partial oxidation.

The driving force for the separation of extract and raffinate is the difference in the mass density (g/cm$^3$) between the two phases. A high mass density difference of the two liquid phases eases phase separation and reduces emulsion formation.

Advantageously, organic solvents whose mass density in kg/m$^3$ differs from the mass density of water (likewise in kg/m$^3$) by $\geq 25$ kg/m$^3$, preferably by $\geq 50$ kg/m$^3$ (based on the pressure employed in the extraction and the temperature employed in the extraction) are therefore used for the extraction to be performed in accordance with the invention. In general, the aforementioned mass density difference will, however, be $\leq 250$ kg/m$^3$, generally $\leq 150$ kg/m$^3$.

In addition, it is favorable for the process according to the invention where the dynamic viscosity of the organic extractant under the extraction conditions is $\leq 100$ mPa·s, preferably $\leq 50$ mPa·s. In general, the aforementioned dynamic viscosity will, however, be $\geq 1$ mPa·s. Dynamic viscosities particularly favorable in accordance with the invention are those in the range from 2 to 10 mPa·s.

It is also advantageous in the process according to the invention when the interface tension between the two fluid phases is comparatively high. Against the background of the statements made so far, extractants suitable in accordance with the invention for the acid water extraction include organic liquids whose boiling point at standard pressure (1 atm) is above 150 or above 160° C. Examples include middle oil fractions from paraffin distillation, diphenyl ether, diphenyl, or mixtures of the aforementioned liquids, for example a mixture of from 70 to 75% by weight of diphenyl ether and from 25 to 30% by weight of diphenyl. It is also favorable to use a mixture consisting of a mixture of from 70 to 75% by weight of diphenyl ether and from 25 to 30% by weight of diphenyl, and also, based on the mixture, from 0.1 to 25% by weight of % o-dimethyl phthalate.

Organic solvents particularly preferred in accordance with the invention for the acid water extraction are the esters of aliphatic or aromatic mono- or dicarboxylic acids (especially when both carboxyl groups are esterified) whose alcoholic component comprises from 1 to 8 carbon atoms and whose carboxylic acid component comprises from 5 to 20 carbon atoms. The alcoholic component preferably has only two hydroxyl groups or only one hydroxyl group before the esterification. The alcoholic component preferably comprises monohydric (one OH group) or dihydric (two OH groups) alkanols. Advantageously, the number of carbon atoms of the alcoholic component (especially in the case of monohydric or dihydric alkanols) is from 1 to 6, more preferably from 1 to 4 and most preferably 1 or 2. The aliphatic or aromatic mono- or dicarboxylic acids comprise advantageously from 5 to 15 carbon atoms, preferably from 5 to 10 carbon atoms and more preferably from 6 to 8 carbon atoms (especially in the case of a respective esterification (in the diester case too) with alkanols having from 1 to 4 or having 1 or 2 carbon atoms). Dicarboxylic acids are preferred over monocarboxylic acids as the acid component of the relevant esters (especially when both carboxyl groups are esterified). Phthalic acid, isophthalic acid and terephthalic acid and also adipic acid are acid components which are very particularly preferred in accordance with the invention for the relevant esters. The latter is especially true in the case of the dialkyl esters ($C_1$- to $C_8$-alkyl, advantageously $C_1$- to $C_6$-alkyl, very particularly advantageously $C_1$- to $C_4$-alkyl and even better $C_1$- or $C_2$-alkyl). In other words, extractants very particularly favorable for the process according to the invention are dimethyl phthalate, diethyl phthalate (e.g. Palatinol® A from BASF Aktiengesell-schaft), dimethyl isophthalate, diethyl isophthalate, dimethyl terephthalate, diethyl terephthalate, dimethyl adipate and diethyl adipate. Further esters suitable for the inventive acid water extraction are the triesters of phosphoric acid, for example tributyl phosphate or tricresyl phosphate. Useful cresyl radicals include ortho-cresyl, meta-cresyl and para-cresyl. Also useful as extractants for the inventive acid water extraction are esters of acrylic acid and branched or linear monohydric $C_6$- to $C_{12}$-alkanols (e.g. 2-propylheptyl acrylate or 2-ethylhexyl acrylate), and also mono- and diesters of maleic acid and monohydric $C_4$- to $C_{1-10}$-alkanols. At the same time, preference is given in accordance with the invention, among all aforementioned extractants, to those which, at standard pressure, have a boiling point above 150° C. or above 160° C., or above 170° C., or above 180° C., or above 190° C.

In general, the acid water to be extracted will comprise, as well as acrylic acid and water, acetic acid as a further constituent (generally the third greatest constituent in % by weight based on the total amount of the acid water). Depending on the manner in which the partial oxidation is performed (catalyst selected, steam content of the reaction mixture, temperature of the partial oxidation), the acid water may comprise up to 10% by weight, or up to 5% by weight (frequently from 2 to 8% by weight) or more of acetic acid. Frequently, the acid water comprises about twice the proportion by weight of acrylic acid based on the proportion by weight of acetic acid. The contents of the other possible acidic secondary components are normally significantly lower. Preference is therefore given in accordance with the invention to those extractants which preferentially absorb acrylic acid compared to acetic acid. These extractants include in particular diethyl phthalate.

It is also advantageously in accordance with the invention when the extractant does not react with water under the extraction conditions and has only a low solubility in water. For example, diethyl phthalate is particularly hydrolysis-stable. A further advantage of diethyl phthalate is its comparatively high boiling point at standard pressure (1 atm), which, advantageously in accordance with the invention for extractants (organic solvents) to be used, is $\geq 200°$ C., better $\geq 225°$ C. and even better $\geq 250°$ C.

In addition, it has a comparatively low solubility in water (this also reduces the extractant losses). In general, the acid water is obtained in the fractional condensation of the product gas mixture to be performed in accordance with the invention with a temperature of from 50 to 80° C., preferably from 60 to 70° C. In other words, it is normally withdrawn via the second liquid phase draw (preferably a side draw) with this temperature (the lower the temperature, the lower the requirement for polymerization inhibitor; in favorable cases, there is no need to separately add one to the acid water, extractant, raffinate and/or extract). Appropriately from an application point of view, the extraction will therefore also be performed in this temperature range. In other words, advantageously in accordance with the invention, the extractant will be conducted essentially with its aforementioned temperature into the extraction unit, preferably an extraction column (more preferably a column with structured packing, advantageously Montz-Pak B1-350). Advantageously, it is fed into the extraction column from the bottom, and the extractant of higher specific gravity (advantageously diethyl phthalate) is introduced from the top. Typically, the temperature of the extractant introduced will not be very different from that of the acid water fed in. Typically, the magnitude of this temperature difference is $\geq 0°$ C. and $\leq 20°$ C., preferably $\geq 0°$ C. and $\leq 15°$ C. and in many cases $\geq 0°$ C. and $\leq 10°$ C. The pressure of the acid water withdrawn from the condensation column is, at the withdrawal point, typically in accordance with the invention from >1 to 1.5 bar, frequently 2 bar. The acid water withdrawn is conducted into the extraction column by means of a pump. The conveying pressure may, for example, be from 2 to 6 bar. The working pressure in the extraction column is selected in accordance with the invention such that it does not require any additional pump in order to convey the organic extract into the first stripping column. In principle, the acid water extraction can, though, also be performed at higher or lower temperatures and at higher or lower pressures. When an extraction column is put into operation, the procedure will be, appropriately from an application point of view, initially to fill the extraction column with acid water and then, as described above, to introduce the organic extractant in droplet form, advantageously at the top of the extraction column. The acid water (the preferably continuous phase) can in principle be fed in directly via an appropriate feed nozzle. In principle, the acid water may, though, also be fed in via a feed tube having one (or more) passage orifice(s) in its wall (diameter of the passage orifices is typically from 5 to 10 mm).

As already mentioned, the extraction column is, appropriately from an application point of view, manufactured from stainless steel. Typical wall thicknesses are from 5 to 20 mm. The extraction column is normally thermally insulated on the outside in a conventional manner.

The ratio V of the flow rates of organic extractant (E; in kg/h) and acid water (S; in kg/h) fed to the extraction column, i.e. E:S, in the process according to the invention may be from 0.05 to 20, preferably from 0.1 to 10, better from 0.8 to 1.2 and more preferably 1:1.

The acid water depleted (extracted) in acrylic acid is normally sent to its disposal (for example incinerated or conducted into a water treatment plant). Typically in accordance with the invention, it leaves the extraction column at its top (as raffinate), while the organic extract comprising the acrylic acid typically leaves the extraction column at the bottom.

The removal of the acrylic acid from the organic extract, whose withdrawal temperature from the extraction column corresponds essentially to the feed temperature of the acid water into the extraction column, can in principle be undertaken using different thermal separation processes or else using combinations of such thermal separation processes.

A suitable removal variant is crystallative removal. Possible crystallization processes include all of those recommended in DE-A 19838845 and in DE-A 10 2005 015 637. The reason for the preference for crystallative removal is that crystallization, in contrast to other thermal separation processes, is a distinct separation process. In other words, the composition of the acrylic acid crystals which form is largely independent (in the ideal case there is complete independence) of the composition of the liquid phase, the liquid extract. In contrast, an indistinct thermal separation process is one in which the composition of the phase which forms when the separation process is employed and comprises the target product in enriched form is markedly dependent upon the composition of the mixture to be separated. In other words, in the distinct separation process, a single establishment of equilibrium is sufficient in thermodynamic theory in order to obtain the pure target product, while repeated successive establishment of the thermodynamic equilibrium is required for this purpose in indistinct separation processes. Crystallization processes which are particularly suitable in accordance with the invention for the purpose of removing the acrylic acid from the extract are suspension crystallization and layer crystallization.

Very particularly advantageously in accordance with the invention (especially when the extractant used is one whose boiling point (at standard pressure) is at least 60° C., preferably at least 80° C. and most preferably at least 100° C. above the corresponding boiling point of acrylic acid (=141° C.)), the removal of the acrylic acid from the extract will be undertaken by desorption. The desorption unit used will typically be a column having separating internals. Useful such column internals include in principle all known separating internals. These include in particular trays, structured packings and/or random packings. Among the mass transfer trays, preference is given to bubble-cap trays, sieve trays (e.g. forced sieve trays or trickle sieve trays (dual-flow trays)), valve trays and/or Thormann trays (i.e. Thormann® trays). Among the random packings, preference is given to those comprising rings, helices, saddles, Raschig, Intos or Pall rings, barrel or Intalox saddles, Top-Pak etc., or braids. Very particular preference is given to dual-flow trays and/or Thormann trays. Among the Thormann trays, the single-flow Thormann trays are preferred. When dual-flow trays and Thormann trays are used, the dual-flow trays are most preferably used in the lower section of the desorption unit and the Thormann trays in the upper section of the desorption unit. In general, from 5 to 10 theoretical plates in the desorption unit are sufficient. In principle, the desorption can be brought about exclusively by lowering the pressure. Very particularly advantageously from an application point of view, the partial pressure of the acrylic acid to be desorbed is lowered by diluting with a gas which is uncondensable under the desorption conditions (the boiling point of the stripping gas at 1 atm is preferably at least 50° C. below the boiling point of water) and essentially inert (with respect to chemical change). In other words, the removal of the acrylic acid from the extract phase of the acid water extraction is most preferably undertaken by stripping by means of a gas (by stripping-out with a gas). In other words, the passage of a gas through the extract results in the acrylic acid being absorbed into the gas and conducted out of the extract. The driving force behind this process is that the vapor pressure of the acrylic acid to be removed from the extract is greater than its partial pressure in the gas, so that acrylic acid is transferred from the extract into the gas. Advantageously, the extract is conducted against the flow direction of the stripping gas (i.e. in countercurrent) for the purpose of stripping. In other words, the extract is advantageously introduced at the top of the stripping column and the stripping gas is conducted into the stripping column at the bottom. Very particularly advantageously, the stripping gas used is the residual gas (or residual gas mixture) conducted out at the top of the rectification column, or a portion of this residual gas with identical or different composition to the overall residual gas, or gas whose composition corresponds to one or more inert constituents of the residual gas (for example steam, $N_2$, $CO_2$, and/or air). The use, preferred in accordance with the invention, of residual gas mixture as stripping gas has the advantage that, firstly, no additional stripping gas (which would also have to be disposed of later) need be provided and, secondly, a stripping gas which does not comprise any constituents extraneous to the overall removal process of the acrylic acid from the product gas mixture of the partial oxidation is thus used. In general, residual gas consists predominantly of the inert diluent gases used for the partial oxidation of the $C_3$ precursor of acrylic acid (remain essentially chemically unchanged in the partial oxidation) and also steam which is typically formed as a by-product in the partial oxidation and may have been added as a diluent gas, and carbon oxides formed by undesired complete oxidation as a side reaction (frequently, a portion of the residual gas which has residual gas mixture composition is recycled as diluent gas into the partial oxidation; this shall be referred to in this document as partial oxidation cycle gas or cycle gas). In some cases, it still comprises small amounts of molecular oxygen unconsumed in the partial oxidation (residual oxygen, which is advantageous (for example for the avoidance of undesired polymer formation)) and/or of unconverted $C_3$ precursors and/or unconverted intermediate. The inert diluent gases used in the partial oxidation (for example $N_2$, $CO_2$, $H_2O$ and/or saturated hydrocarbons, etc.) are helpful firstly in absorbing the heat of reaction released in the partial oxidation and secondly generally ensure safe operation of the heterogeneously catalyzed gas phase partial oxidation of the $C_3$ precursor by keeping the reaction mixture either outside the explosion range or within a region of the explosive range which can still be controlled safely (cf., for example, DE-A 197 40 253, DE-A 197 40 252, DE-A 102 43 625, DE-A 103 32 758 and WO 2004/035514).

When dual-flow trays are used as separating internals in the desorption column (stripping column), the whole diameter (the diameter of the passage orifices in the trays) is generally from 8 to 50 mm, preferably from 10 to 35 mm. The whole diameter preferably increases from the top downward. The tray separation (the trays are typically arranged equidistantly) is frequently from 300 to 800 mm, in many cases from 400 to 600 mm and frequently 500 mm. The desorption unit, as already stated, is typically manufactured from austenitic steel, preferably from the material 1.4571 (to DIN EN 10020).

The column feed of extracts to be stripped is in the upper region of the desorption unit, preferably at its uppermost tray (theoretical plate). Appropriately from an application point of view, the extract is heated beforehand (typically to temperatures of from 80 to 120° C., frequently approx. 100° C.). Internal and/or external indirect heat exchangers of conventional design (for example Robert evaporators, forced-circular tube bundle heat transferers, forced-circulation tube bundle flash heat transferers, plate heat transferers, etc; cf., for example, EP-A 854 129) and/or via jacket heating (the heat carrier used is advantageously steam obtained with the waste heat of the partial oxidation) are advantageously used to additionally supply heat to the bottom of the stripping column (of the desorption column). It is preferably effected via external circulation evaporators with natural or forced circulation. More preferably, external circulation evaporators with forced circulation (especially flash circulation) are used. The use of a plurality of evaporators connected in series or parallel is possible (typical bottom temperatures are from 145 to 165° C., frequently approx. 155° C.).

The inert stripping gas which is uncondensable under the desorption conditions employed is advantageously introduced directly into the bottom of the desorption unit. The feed from the external heat transferer (in which the required heat is supplied to bottoms liquid withdrawn beforehand) is advantageously undertaken at one of the lower column trays (theoretical plates) (preferably in the region of theoretical plates 2 to 4 from the bottom) or lower. The essentially acrylic acid-free extractant obtained in the column bottom of the desorption column is advantageously recycled to the top of the acid water extraction.

Since it normally has an elevated temperature compared to the extract obtained in the extraction unit, it is appropriate to conduct the extract to be conducted from the extraction to the stripping column and the extractant to be recycled from the bottom of the stripping column to the extraction (any active polymerization inhibition of extraction and stripping column required would, owing to the recycling, advantageously be undertaken into the bottom of the stripping column; for example by means of MEHQ and/or PTZ, when the stripping gas comprises molecular oxygen) in indirect heat exchange through an indirect heat transferer of conventional design (tube bundle heat transferer or plate heat transferer) in order to heat the extract and to cool the extractant. Subsequently, the extractant will normally additionally be brought to its use temperature in the acid water extraction in an indirect heat transferer by means, for example, of water cooling. Based on the extractant stream recycled out of the bottom of the stripping column into the extraction, from 0.01 to 1% by weight of the bottoms liquid of the stripping column will normally additionally be discharged (purge stream) (beyond the aforementioned water cooling, an appropriate stream of fresh extractant will normally be supplemented in the extractant recycle stream). This purge stream can be disposed of (for example incinerated together with residual gas) or be worked up by rectification and converted to fresh extractant.

The stripping gas is preferably conducted into the stripping column with a temperature which largely corresponds at least to that of the bottoms liquid in the stripping column (in general, the two temperatures will differ by not more than 30° C., better not more than 20° C.). When residual gas is used as stripping gas, it may, for example, thus be brought to the aforementioned temperature by compressing it to an elevated pressure. Advantageously, this compression, together with cycle gas, can be effected to a pressure which is also suitable for the recycling of the residual gas into the $C_3$ precursor partial oxidation (typically with the aid of a radial compressor). Typically, the aforementioned pressure is from 2 to 4 bar, frequently from 2.5 to 3.5 bar (at a residual gas pressure of typically >1 and ≦1.5 bar).

Based on 1 kg of extract, the amount of stripping gas required to strip it free of acrylic acid is typically from 1.5 to 2.5 $m^3$ (STP) of stripping gas. Typical loadings of the stripping gas with acrylic acid are (at the top of the stripping column) from 2 to 6% by weight.

In principle, the heat input into the bottom of the stripping column can be reduced with increasing amount of stripping gas used. One reason for the preference for removal of the acrylic acid from the extract by stripping with an inert stripping gas which is typically uncondensable under the desorption conditions is that it is a particularly efficient removal method which is comparatively undemanding in energy and apparatus terms. In addition, in contrast to, for example, crystallative or rectificative removal from the extract, it is associated with the advantage that it does not generate any additional liquid phase which comprises acrylic acid in elevated concentration and requires the cost and inconvenience of an additional marked polymerization inhibition.

The aforementioned fact is attributable not least to the fact that the acrylic acid-laden stripping gas, especially when residual gas was used for the stripping, can be recycled as such into the condensation column (which is used for the fractional condensation of the product gas mixture of the partial oxidation). Appropriately, such a recycling is effected below the first side draw into the condensation column. Advantageously, the recycling will be undertaken directly in the bottom space of the condensation column. In principle, it can be effected directly into the bottoms liquid.

The present application therefore comprises, in particular, a process according to the invention wherein acrylic acid present at least in a portion (advantageously a portion of at least 25% by weight, better at least 50% by weight, preferably at least 75% by weight, or the entirety) of acid water not recycled into the condensation column is taken up from the acid water into an organic solvent by extraction with the organic solvent to form an organic extract comprising acrylic acid, then the acrylic acid is removed from the organic extract by stripping with a stripping gas and the acrylic acid-laden stripping gas is recycled into the condensation column. In principle, the recycling of the acrylic acid present in the laden stripping gas into the condensation column could also be effected in condensed form. This condensed acrylic acid could, though, also be sent to the further purification thereof combined with the crude acrylic acid withdrawn from the condensation column.

Very particularly advantageously, in the process according to the process, the acrylic acid-laden stripping gas (or at least a portion thereof) will, however, be used in order to, in a second stripping column, likewise strip free acrylic acid still present in the bottoms liquid withdrawn from the condensation column (and only then will it be recycled into the condensation column), before the bottoms liquid is sent to disposal. Advantageously in accordance with the invention, the laden stripping gas of this second stripping is also subjected to (countercurrent) rectification, as has already been described in WO 2004/035514 and in DE-A 103 32 758 (but with immediate use of residual gas as stripping gas) (and only then is it recycled into the condensation column).

The bottom space in the condensation column used in the process according to the invention (or quite generally in a column having separating internals), the space below the lowermost separating internal (for example trays, structured packings and random packings which enlarge the interface between the phases conducted in countercurrent in the separation column) within the condensation column.

The so-called bottoms liquid, which comprises especially those constituents whose boiling point at standard pressure (1 atm) is above the boiling point of acrylic acid, collects therein. These are firstly by-products having a higher boiling point than acrylic acid, for example maleic anhydride, secondary components such as phenothiazine, which are added as polymerization inhibitors, but also conversion products which are only formed from the constituents in the course of the fractional condensation of the product gas stream of the partial oxidation. These conversion products include in particular free-radical polymers of acrylic acid which, in spite of the polymerization inhibition, form in an undesired manner. Higher molecular weight compounds which are formed by condensation reactions of different constituents of the product gas mixture of the partial oxidation are also included therein. They include not least the Michael adducts which are formed by reversible Michael addition of acrylic acid to itself and to the acrylic acid dimers ("diacrylic acid") or oligomers which form in this way (in this document, the term "acrylic acid oligomers" therefore always means the corresponding Michael adducts and not acrylic acid oligomers formed by free-radical polymerization). The action of elevated temperature with simultaneous removal of the acrylic acid formed (for example by "stripping" with a gas which is preferably (chemically) inert and uncondensable under the appropriate conditions) allows the Michael addition to be reversed. However, monomeric acrylic acid itself is also still a constituent of the bottoms liquid in the condensation column to a not inconsiderable degree, which means that it is worth stripping it free. Since the bottoms liquid of the condensation column, though, also comprises by-products which, at standard pressure, boil at only slightly higher temperatures than acrylic acid (for example benzaldehyde, furfurals and maleic anhydride), it is advantageous to subject the laden stripping gas of this second stripping (before, for example, it is recycled into the condensation column) additionally to a (countercurrent) rectification (i.e. a countercurrent flow of reflux liquid) (appropriately in the same column), which causes an improved purity of the acrylic acid-laden second stripping gas.

The recycling of the first laden stripping gas and/or of the second laden stripping gas into the condensation column need not necessarily be effected by a direct route.

Instead, the first laden stripping gas and/or the second laden stripping gas may also be mixed at least partly or completely with product gas mixture and the resulting gas mixture can be conducted into the condensation column.

The combination can be effected before, during and/or after any direct and/or indirect cooling of the product gas mixture of the gas phase partial oxidation to be performed.

Hereinafter, for reasons of differentiation, the acrylic acid-laden stripping gas from the extract stripping will be referred to as "first laden gas" and the acrylic acid-laden (preferably rectified) stripping gas from the (condensation column) bottoms stripping as "second laden gas" (correspondingly, the extract stripping will be referred to as "first stripping" and the bottoms stripping as "second stripping", etc.). In general, the first laden gas leaves the extract stripping with a pressure of from 1.5 to 3.5 bar, frequently from 2 to 3 bar, for example 2.5 bar. Its temperature is typically approx. 10° C. below that temperature with which the extract is introduced into the first stripping column. Typical temperatures of the first laden gas are from 65 to 95° C., frequently from 75 to 95° C., or 85° C.

For the performance of the second stripping (including the rectification of the stripping gas), useful columns are in principle all columns with separating internals, possible internals being, for example, structured packings, random packings and/or trays. In principle, it is also possible to use columns with rotating inserts, known as rotation columns, which spray the reflux liquid into drops. Preference is given in accordance with the invention to using, as the second stripping column, one which comprises only trays and/or structured packings. The trays used are advantageously dual-flow trays, and the stripping column particularly advantageously comprises exclusively dual-flow trays as separating internals.

In this document, dual-flow trays shall be understood to mean plates with simple passages (holes, slots, etc.). The gas ascending in the second stripping column and the reflux liquid descending in the second stripping column meet flowing in opposite directions through the same passages. The cross section of the passages is adjusted in a manner known per se to the loading of the second stripping column. When it is too small, the ascending gas flows through the passages with such a high speed that the reflux liquid descending in the stripping column is entrained essentially without separating action. When the cross section of the passages is too great, ascending gas and descending reflux move past one another essentially without exchange and the tray is at risk of running dry. Typically, dual-flow trays do not have any drainpipe which connects them to the next tray. Of course, each dual-flow tray can conclude flush with the walls of the second stripping column.

However, it can also be connected to the walls via connecting elements. In contrast to hydraulically sealed cross flow trays, dual-flow trays run dry with increasing loading of the second stripping column.

Appropriately in accordance with the invention, the dual-flow tray stripping column usable for the second stripping (including the rectification addressed) may comprise up to 60 dual-flow trays. Advantageously, these have an orifice ratio (the ratio D:U formed from the proportion of the area of the tray which is permeable for the cleavage gas (D) and the total area of the tray (U)) of from 10 to 20%, preferably from 10 to 15%.

The passages of the dual-flow trays are preferably circular holes with a circle diameter uniform within the tray. The latter is appropriately from 10 to 30 mm. In the upper part of the column, it is advantageously from 10 to 20 mm or from 10 to 15 mm, and in the lower part of the column it is advantageously from 20 to 30 mm. Moreover, the circular holes are preferably arranged uniformly in strict triangular pitch over the individual dual-flow trays (cf. DE-A 102 30 219). Moreover, the punching burr of the passage orifices punched out in the dual-flow trays in the second stripping column preferably points downward. Customarily, the dual-flow trays in the second stripping column are arranged equidistantly. Typically, the tray separation is from 300 mm to 500 mm. A tray separation of 400 mm is also favorable in accordance with the invention. Appropriately, the bottoms liquid to be stripped (it may also be used beforehand for the direct cooling of the product gas mixture of the partial oxidation and/or may have been supplemented by high boiler fraction withdrawn in the lower region of the condensation column) is fed in at the fourth to tenth dual-flow tray of the second stripping column (calculated from the bottom). The bottom temperature in the second stripping column is kept advantageously at from 150 to 190° C., preferably from 160 to 180° C. The working pressure in the second stripping column will normally be from >1 to 3 bar, frequently from 1.5 to 2.5 bar.

The energy input required in the second stripping column is advantageously supplied with the aid of an external force-circulation tube bundle flash evaporator to which bottoms liquid withdrawn from the second stripping column is supplied for the purpose of superheating it and is then recycled thus superheated into the second stripping column (cf. DE-A 103 32 758). In principle, it is also possible at this point to use a pure forced-circulation evaporator or a natural-circulation evaporator, for example a Robert evaporator, which can also be integrated into the second stripping column.

The second stripping column itself is (like the condensation column and the first stripping column too), appropriately from an application point of view, thermally insulated against the environment.

The reflux liquid can be generated by direct and/or indirect cooling. Advantageously in accordance with the invention, the method of direct cooling is employed. To this end, in the simplest manner, the gas flowing through the last tray (theoretical plate) is fed to a quench apparatus which may, for example, be integrated into the second stripping column (attached to the separating section) delimited by means of a chimney tray from the separating internals of the second stripping column. In principle, the quench apparatus may, though, also be disposed spatially outside the second stripping column. Useful such quench apparatus includes all apparatus known for this purpose in the prior art (for example spray scrubbers, Venturi scrubbers, bubble columns or other apparatus with sprayed surfaces), preference being given to using Venturi scrubbers or spray coolers. Advantageously, a countercurrent apparatus (for example one with an impingement plate nozzle) is used. For the indirect cooling of the quench liquid, it is typically conducted through an (indirect) heat transferer or heat exchanger. In this regard, suitable apparatus is all common heat transferers or heat exchangers. Preferred apparatus includes tube bundle heat exchangers, plate heat exchangers and air coolers. Suitable cooling media are air in the appropriate air cooler, and cooling liquids, especially water (for example surface water), in the other cooling apparatus. Appropriately from an application point of view, the quench liquid used (also referred to hereinafter as "quench liquid 0") is a portion of the condensate formed in the quenching. The other portion of the condensate formed in the quenching is recycled essentially as reflux liquid to the uppermost tray (theoretical plate) of the second stripping column (a small portion of the condensate can also be branched off at this point and fed to the bottoms liquid withdrawn from the condensation column and combined with it; a portion of the resulting mixture can be used as quench liquid 1 which is yet to be introduced in the further course of this document; another portion of this mixture forms the feed to the second stripping column and the remaining (comparatively small) residual amount of this mixture is combined with the remaining portion of the condensate and, in this combination, then firstly forms the reflux liquid to the uppermost tray (theoretical plate) of the second stripping column and secondly the quench liquid 0). Typically, the temperature of the quench liquid 0 immediately before its use for quenching is about 40° C., whereas the reflux liquid is typically recycled at about 80° C. The mass ratio of recycled reflux liquid to bottoms liquid fed to the second stripping column (and if appropriate high boiler liquid) is typically $\geq 2$. It is frequently from 2 to 10 and preferably from 4 to 8.

Of course, the second stripping column (like all other apparatus in which liquid phases having significant acrylic acid contents are conducted) has to be operated with polymerization inhibition. Such polymerization inhibitors used for this purpose are in principle all polymerization inhibitors known in the prior art.

Examples thereof include phenothiazine (PTZ) and p-methoxyphenol (MEHQ). Frequently, these two are used in combination. Appropriately for this purpose, they are added dissolved in pure acrylic acid. MEHQ is preferably metered in as a melt.

However, the polymerization inhibition of the quench circuit 0 and of the second stripping column can be accomplished in a particularly elegant manner by adding to the quench circuit 0 a portion of the bottoms liquid (and if appropriate high boiler fraction) which has been polymerization-inhibited, i.e. comprises polymerization inhibitors, and has been conducted out of the condensation column. Typically, this quench liquid 0 thus comprises, for example, from 0.01 to 0.1% by weight of MEHQ and from 0.01 to 0.5% by weight of PTZ. The molecular oxygen typically still present in the first laden gas (which functions as the stripping gas for the second stripping column) additionally promotes the polymerization inhibition.

A portion of the bottoms liquid which occurs in the bottom of the second stripping column is discharged and disposed of continuously. Addition of an organic solvent, for example of methanol, keeps the most nonvolatile residue fluid if required. Instead of methanol, it is also possible to use other hydrophilic organic liquids, for example ethanol, or those recommended in WO 2004/035514 (or mixtures of such liquids). Based on the feed stream of bottoms liquid fed out of the condensation column, the aforementioned discharge stream is from approx. 10 or 20 to 30% by weight. Appropriately from an application point of view, the discharge stream is branched off from the stream which leaves the forced-circulation flash evaporator in superheated form and supplies the second stripping column with energy. It is degassed and, for example diluted with methanol, sent, for example, to residue incineration.

The second laden gas which leaves the quench circuit 0 in cooled form (typical temperatures are from 70° C. to 90° C.) can then be recycled as such into the condensation column (at this point, it should be emphasized that typically from 1 to 10 $m^3$ (STP) of first laden gas are used as stripping gas in the second stripping column based on 1 kg of bottoms liquid fed from the condensation column; typically, the liquid is present in the bottom of the second stripping column in the boiling state). Its acrylic acid content is typically from 15 to 20%. In principle, the recycling of the acrylic acid present therein into the condensation column could also be effected in condensed form. Such an acrylic acid condensate can, though, also be fed to further purification combined with the crude acrylic acid withdrawn from the condensation column. Preference is given in accordance with the invention to acrylic acid recycling into the condensation column as a constituent of the second laden gas as such, i.e. in gaseous form (in principle, the recycling can also be effected in partly condensed form).

The recycling of the second laden gas into the condensation column (all statements apply equally to recycling of the first laden gas as such into the condensation column) is preferably undertaken below the first side draw (in principle, it can also be effected into the direct cooling circuit of the product gas mixture of the gas phase partial oxidation). Appropriately from an application point of view, it is effected into the bottom space of the condensation column. This recycling can be undertaken either immersed into the bottoms liquid or above the liquid level of the bottoms liquid and below the first tray (theoretical plate) of the condensation column. The bottom space of the condensation column advantageously comprises a droplet separator (for example a centrifugal droplet separator), in order to suppress entrainment of bottoms liquid droplets by ascending gas. Moreover, the bottom space can be separated from the lowermost separating internal by a first chimney tray.

The residence time of the bottoms liquid fed to the second stripping column from the condensation column (if appropriate including high boiler fraction withdrawn) in the second stripping apparatus should typically be from 0.5 to 4 h (for a high boiler secondary component discharged finally). Of course, redissociation catalysts for the redissociation of the acrylic acid oligomers can be metered into the bottom of the second stripping apparatus, as recommended, for example, by WO 2004/035514.

It will be appreciated that it is also possible to add to the bottom of the second stripping column assistants such as Komad®313 from Mol (Hungary) and/or dispersants (for example those of EP-A 1 062 197 and/or of U.S. Pat. No. 3,271,296), for example tertiary amines (e.g. trimethylamine, triethylamine, N,N,N',N'-tetramethyl-1,6-hexanediamine and pentamethyldiethylenetriamine) which reduce the fouling in the indirect heat exchanger which ensures the required energy supply and promote the acrylic acid yield. The amounts added may be from 0.1 to 10% by weight based on the bottoms of the second stripping column. Since the substances are advantageously already high-boiling substances or these additives form them with acrylic acid, they are not stripped out at the same time.

One reason for the advantage of the inventive procedures described is that they enable an increase in the yield of acrylic acid without significantly reducing the purity of the crude acrylic acid withdrawn via the first side draw. This relates not least to the stripping variant described, even when residual gas from the condensation column is used as described for the purpose of stripping.

In this case, the purity both of the first and of the second laden gas with regard to secondary components which are disruptive in a subsequent use of acrylic acid (for example for the preparation of water-superabsorbing polymers) is already so good that the acrylic acid present therein can even be taken up directly from the gas phase of the first or second laden gas (from the entirety or only from a portion of the first and/or second laden gas in each case) into the aqueous solution of a metal hydroxide (for example of an alkali metal hydroxide and/or alkaline earth metal hydroxide, e.g. NaOH, KOH, $Ca(OH)_2$ and/or $Mg(OH)_2$) (for example in a completely corresponding manner to the procedure described in WO 2003/095410), and the aqueous solution of sodium acrylate which results, for example, in the case of absorption into, for example, aqueous sodium hydroxide solution can be used, for example, directly for the preparation of water-superabsorbing polymers by appropriate free-radical polymerization (on this subject, see also WO 2003/014172).

This is not least because by-products such as formaldehyde and formic acid normally remain preferentially in the aqueous phase of the acid water. The first or second laden gas freed of acrylic acid by, for example, countercurrent scrubbing with aqueous sodium hydroxide solution (or another of the aforementioned aqueous metal hydroxide solutions) in a column comprising separating internals (trays, random packings and/or structured packings) can subsequently be recycled into the extract stripping and/or sent to incineration.

Typically, the acrylic acid-comprising product gas mixture of a heterogeneously catalyzed gas phase partial oxidation of $C_3$ precursors of acrylic acid with molecular oxygen over solid-state catalysts may, for example, have the following contents (especially when the $C_3$ precursor used is propylene):

| | |
|---|---|
| 1 to 30% by wt. of | acrylic acid, |
| 0.05 to 10% by wt. of | molecular oxygen, |
| 1 to 30% by wt. of | water, |
| >0 to 5% by wt. of | acetic acid, |
| >0 to 3% by wt. of | propionic acid, |
| >0 to 1% by wt. of | maleic acid and/or maleic anhydride, |
| 0 to 2% by wt. of | acrolein, |
| 0 to 1% by wt. of | formaldehyde, |
| >0 to 1% by wt. of | furfurals, |
| >0 to 0.5% by wt. of | benzaldehyde, |
| 0 to 1% by wt. of | propylene, and, as the remainder, essentially inert gases, for example nitrogen, carbon monoxide, carbon dioxide, methane and/or propane. |

Typically, the product gas mixture comprises, based on acrylic acid present, $\geq 0.005$ mol %, frequently $\geq 0.03$ mol %, of furfurals. In general, the furfural content on this basis is, however, <3 mol %.

The gas phase partial oxidation itself can be performed as described in the prior art. Proceeding from propylene, the gas phase partial oxidation can be performed, for example, in two successive oxidation stages as described in EP-A 700 714 and in EP-A 700 893. However, it will be appreciated that the gas phase partial oxidations cited in DE-A 197 40 253 and in DE-A 197 40 252 may also be used.

For the purpose of a small amount of secondary components formed, the propylene gas phase partial oxidation is preferably performed as described in DE-A 101 48 566. For this purpose, the propylene source used may be polymergrade propylene or chemical-grade propylene according to DE-A 102 32 748. When the $C_3$ precursor used is propane, the partial oxidation may be performed as described in DE-A 102 45 585.

However, the gas phase partial oxidation can in principle also be performed as described in the documents US 2006/0161019, WO 2006/092410, WO 2006/002703, WO 2006/002713, WO 2005/113127, DE-A 10 2004 021 763, EP-A 1 611 076, WO 2005/108342, EP-A 1 656 335, EP-A 1 656 335, EP-A 1 682 478, EP-A 1 682 477, German applications 10 2006 054 214.2 and 10 2006 024 901.1, EP-A 1 611 080, EP-A 1 734 030, German applications 10 2006 000 996.7, 10 2005 062 026.4, 10 2005 062 010.8, international application PCT/EP 2006/065416, PCT/EP 2006/067784 and PCT/EP 2006/067080.

Frequently, the temperature of the product gas mixture leaving the gas phase partial oxidation is from 150 to 350° C., in many cases from 200 to 300° C., sometimes up to 500° C.

Appropriately from an application point of view, the hot product mixture is subsequently cooled in a quench apparatus 1 by direct cooling generally to a temperature of from 100 to 180° C., before it is passed, advantageously from an application point of view together with the quench liquid 1 used, for the purpose of fractional condensation, preferably into the lower section (preferably at the lowermost section, for example the bottom space) of a condensation column comprising separating internals. Preferred condensation column internals are in principle all common internals, especially trays, structured packings and/or random packings. Among the trays, preference is given to bubble-cap trays, sieve trays, valve trays and/or dual-flow trays. Typically, the total number of separating trays in a tray column is from 20 to 100, frequently from 20 to 80 and preferably from 50 to 80.

Preferably in accordance with the invention, the condensation column is one which comprises, as separating internals, from the bottom upward, first dual-flow trays and then hydraulically sealed crossflow trays (e.g. Thormann® trays), as recommended by DE-A 102 43 625, DE-A 199 24 532 and DE-A 102 43 625. The number of dual-flow trays may be from 5 to 60, frequently from 25 to 45, and the number of hydraulically sealed crossflow trays likewise from 5 to 60, frequently from 30 to 50. For the region of acid water formation preferred in accordance with the invention (acrylic acid content of the reflux liquid viewed from the bottom upward generally $\leq 15\%$ by weight, or in some cases $\leq 10\%$ by weight), useful separating internals are preferably valve trays, as described by DE-A 199 24 532 and DE-A 102 43 625. In principle, it would, though, also be possible to use other common separating internals (the individual regions within the condensation column can of course quite generally also be configured in a completely equivalent manner (instead of one on top of another in one column) as a series connection of correspondingly smaller columns, which is why the term "condensation column" used specifically in this document, and also the term "column" used in general in this document, also comprises such series connections of corresponding smaller columns).

The quench apparatus 1 used may be all apparatus known for this purpose in the prior art (for example spray scrubbers, Venturi scrubbers, bubble columns or other apparatus with sprayed surfaces), preference being given to using Venturi scrubbers or spray coolers.

For the indirect cooling or heating of the quench liquid 1, it is, especially in the course of startup, preferably but not necessarily conducted through a heat transferer or heat exchanger. In this regard, all common heat transferers or heat exchangers are suitable. Preference is given to tube bundle heat exchangers, plate heat exchangers and air coolers. Suitable cooling media are air in the corresponding air cooler and cooling liquids, especially water, in the other cooling apparatus.

The quench liquid 1 used may, for example, be bottoms liquid withdrawn from the bottom of the condensation column (if appropriate combined with condensate conducted out of the quench circuit 0), or, via a side draw close to the bottom, high boiler fraction or a mixture of such bottoms liquid and high boiler fraction (especially when the bottom space and the lowermost tray (theoretical plate (the lowermost separating internal)) are separated by a chimney tray). If appropriate, only the proportion of the quench liquid 1 which has been withdrawn from the bottom of the condensation column is conducted through the abovementioned heat exchanger. The temperature of the quench liquid 1 on entry into the quench apparatus 1 is generally appropriately from 90° C. to 120° C.

The introduction point for the quenched product mixture (or which has been cooled in another way or not cooled) of the catalytic gas phase partial oxidation (according to the invention, as described, preferably in a mixture with the quench liquid 1 used for direct cooling) into the condensation column is advantageously in the bottom space of this column, which advantageously comprises an integrated centrifugal droplet separator and is generally separated by a first chimney tray from the lowermost separating internal (appropriately from an application point of view, in this case, high boiler fraction is constantly passed into the bottom of the condensation column via a connecting line or via an overflow). In an exemplary and preferred embodiment (which is described exclusively hereinafter without restricting the general performability), this lowermost separating internal is the first dual-flow tray of a first series of appropriately equidistant dual-flow trays. The chimney tray functions simultaneously as the collecting tray from which condensate (high boiler fraction) is withdrawn continuously and conducted as part of the quench liquid 1 into the quench apparatus 1 or into the bottom space. The first series of dual-flow trays is concluded by a second chimney tray (collecting tray). From this second collecting tray, crude acrylic acid which preferably has a purity of $\geq 90$ or $\geq 95\%$ by weight is withdrawn continuously as a medium boiler fraction in the first side draw.

Appropriately, this crude acrylic acid will be sent to further distillative (rectificative) and/or crystallative further purification stages and at least a portion of the bottoms liquids and/or mother liquors obtained in the course of this distillation (rectification) and/or crystallization will be recycled into the condensation column below the first side draw but above the first collecting tray. This recycling is preferably effected with thermal integration. In other words, cold mother liquor to be recycled is conducted through one or more series-connected indirect heat exchangers (for example spiral heat exchangers), in order to cool therein the crude acrylic acid to be further purified by crystallization, which has been withdrawn from the condensation column and conducted on the opposite side in the heat exchanger. At the same time, this brings about heating of the mother liquor. For this purpose, preference is given to using two plate heat exchangers connected in series.

Appropriately, the crude acrylic acid withdrawn (as the medium boiler fraction) will be sent to a crystallization for the purpose of further purification. The crystallization process to be used is in principle subject to no restriction. The crystallization can be performed continuously or batchwise, in one or more stages, up to any desired purities. If required, it is advantageously possible to add water to the crude acrylic acid to be purified before the crystallization (in general, this then comprises, based on the amount of acrylic acid present, up to 20% by weight or up to 10% by weight, usually up to 5% by weight of water). In the case of elevated aldehyde or other secondary component contents, water addition can be dispensed with, since the aldehydes in this case are capable of assuming the function of water. Very particularly advantageously in accordance with the invention, the water is added in the form of acid water. This leads to an increase in the yield of glacial acrylic acid.

It is surprising that, even in the case of preceding acid water addition to the crude acrylic acid (this measure likewise causes an increase in the acrylic acid yield), esterification-grade acrylic acid (for example for the preparation of n-butyl acrylate, 2-ethylhexyl acrylate, methyl acrylate and ethyl acrylate) which satisfies the highest demands (purity $\geq 98\%$ by weight) can be achieved actually by a single crystallization stage. Appropriately, this crystallization stage is performed as a suspension crystallization, as described in column 10 of DE-A 199 24 532 or in example 1 of DE-A 102 23058 (for example in a cooling-disk crystallizer as described in WO 2006/111565). The acrylic acid crystals formed in the suspension crystallization have a cubic to cuboidal appearance. The length (L) to thickness (D) ratio is typically in the range from L:D=1:1 to L:D=6:1, preferably in the range from 1:1 to 4:1 and more preferably in the range from 1.5:1 to 3.5:1. The thickness D of the crystals is typically in the range from 20 to 600 µm, often from 50 to 300 µm. The length L of the crystals is typically in the range from 50 to 1500 µm, often from 200 to 800 µm. In the case of acrylic acid suitable for esterification, the suspension crystals can be removed from the remaining mother liquor on a centrifuge (for example a 2- or 3-stage pusher centrifuge), in which case the crystals removed are advantageously washed on the centrifuge by means of molten pure crystals. When the suspension crystals are separated from the remaining mother liquor by means of a wash column, for example a melt wash column (for example one according to WO 01/77056, or DE-A 101 56 016, or DE-A 102 23 058, or as described in WO 2006/111565, WO 04/35514, WO 03/41833, WO 02/09839, WO 03/41832, DE-A 100 36 881, WO 02/55469 and WO 03/78378), it is possible by means of a single crystallization stage even to achieve superabsorbent-grade acrylic acid (purity $\geq 99.7 \geq 99.9\%$ by weight), i.e. acrylic acid which is suitable for preparing water-superabsorbing or other polyacrylates. In this case, the entirety of the mother liquor removed is appropriately recycled into the condensation column.

The crystallization can, though, also be performed as a fractional falling-film crystallization, as recommended by EP-A 616 998. This may, for example, comprise two, three or more (for example from 2 to 4) purification stages (falling-film crystallizers suitable in this context may comprise, for example, from 1000 to 1400 crystallization tubes of length from 10 to 15 m and of external diameter from 50 to 100 mm). The mother liquor removed in a higher purification stage can be recycled into one of the preceding purification stages. The mother liquor removed in the first purification stage is advantageously recycled completely into the condensation column. Alternatively to the recycling into one of the preceding purification stages, the mother liquors of the individual purification stages can also be recycled in their entirety into the condensation column. The pure product of the penultimate purification stage can be fed completely or only partly to the last purification stage. When only partial feeding is effected, the remaining residual amount will generally be blended with the pure product of the last purification stage to give the end product which is then ready to use.

Appropriately in accordance with the invention, a portion of the crude acrylic acid withdrawn via the first side draw will be fed to the dual-flow tray disposed below its accompanying collecting tray. Mother liquor which is to be recycled into the condensation if appropriate will generally also be fed to this tray. Before the feeding, the mother liquor will generally, as already described, be heated to a temperature which corresponds to about the withdrawal temperature of the crude acrylic acid with thermal integration.

Another portion of the crude acrylic acid withdrawn via the first side draw will advantageously be heated by from 10 to 15° C. by indirect heat exchange and be recycled into the condensation column above the withdrawal point, preferably immediately below the first subsequent dual-flow tray. This measure has a favorable effect on the acetic acid content of the crude acrylic acid withdrawn.

Above the second collecting tray, there initially follows a second series of appropriately equidistant dual-flow trays which are then succeeded by hydraulically sealed crossflow mass transfer trays (for example Thormann trays or modified Thormann trays according to DE-A 102 43 625), which are appropriately likewise arranged equidistantly. The uppermost dual-flow tray is, if appropriate, modified as the distributor tray. In other words, it has, for example, overflow channels with serrated overflow.

The first of the Thormann trays from the bottom is, appropriately from an application point of view, one in which the liquid running off from the tray runs off through six downcomers configured as tubes. These tubes are sealed hydraulically from the gas space of the next dual-flow tray down. The weir height of the six downcomers, appropriately from an application point of view, decreases in flow direction of the crossflow tray. Advantageously, the hydraulic seal has emptying orifices with impingement plates. The runoff tubes are preferably distributed uniformly in the second half, more preferably in the last third, of the tray cross section (on the opposite side to the feed onto the tray).

The hydraulic sealing is effected into a cup with oblique overflow weir (45° C.).

The crossflow mass transfer trays are concluded by a third chimney tray (collecting tray).

Above the third collecting tray are disposed preferably two-flow valve trays. The principle of valve trays and valve trays useable in accordance with the invention can be found, for example, in Technische Fortschrittsberichte [Technical progress reports], volume 61, Grundlagen der Dimensionierung von Kolonnenböden [Fundamentals of the dimensioning of column trays], p. 96 to 138. They are essentially characterized in that they provide a flow orifice corresponding to the particular loading to the vapor flowing through over a wide loading range. Preference is given in accordance with the invention to using ballast trays. In other words, cages with orifices closed by weights are disposed in the orifices of the tray. Particular preference is given in accordance with the invention to Vv12 valves from Stahl, Viernheim, Germany. Essentially water and constituents less volatile than water condense in the valve tray space. The condensate obtained is acid water.

The acid water is withdrawn continuously in a second side draw from the third collecting tray. A portion of the acid water withdrawn is recycled into the condensation column to the uppermost of the cross flow mass transfer trays. Another portion of the acid water withdrawn is cooled by indirect heat exchange and, split in an appropriate manner, likewise recycled into the condensation column. A cooled portion is recycled into the condensation column to the uppermost valve tray (with a temperature of from 15 to 25° C., preferably from 20 to 25° C.), and the other cooled portion to a valve tray positioned about equidistantly between the third collecting tray and the uppermost valve tray (with a temperature of from 20 to 35° C., preferably from 25 to 30° C.). The amount of acrylic acid present can be removed in accordance with the invention from the remaining amount of acid water withdrawn.

Some of the cooling (which can be undertaken by means of one or more indirect heat exchangers connected in series) is brought about by virtue of the appropriate portion of acid water being conducted through the evaporator of the $C_3$ precursor (e.g. the propylene evaporator), in order to convert $C_3$ precursor stored in liquid form, for example propylene, to the gas phase for the heterogeneously catalyzed gas phase oxidation.

The constituents more volatile than water are drawn in gaseous form as residual gas (or residual gas mixture) at the top of the condensation column and normally recycled into the gas phase partial oxidation at least partly as diluent gas (cycle gas). In order to prevent condensation in the cycle gas compressor, the residual gas mixture is superheated beforehand by indirect heat exchange. The portion of the residual gas mixture which is not circulated is normally sent to incineration. A portion of the (preferably compressed) residual gas mixture is, as already described, advantageously used as stripping gas to remove acrylic acid from the extract and from the bottoms liquid of the condensation column. Advantageously, the gas phase partial oxidation is performed with an excess of molecular oxygen, so that the residual gas mixture and hence the first and the second stripping gas comprise molecular oxygen when residual gas mixture is used as such stripping gas.

For the purpose of polymerization inhibition, a solution of p-methoxyphenol (=MEHQ) in acrylic acid or (preferably in accordance with the invention) an MEHQ melt and (in both cases), if appropriate, additionally a solution of phenothiazine in acrylic acid is fed to the uppermost of the hydraulically sealed crossflow mass transfer trays. The acrylic acid used is preferably pure acrylic acid, as obtained in the further purification of the crude acrylic acid withdrawn. For example, the glacial acrylic acid (pure product) obtained in the course of the crystallizative further purification can be used. This solution is appropriately also used for pure product stabilization.

In addition, in about the middle of the column cross section with the hydraulically sealed mass transfer trays, a solution of phenothiazine (=PTZ) in pure product is fed in.

In principle, the acid water formation can, for example, also be performed beyond a first condensation column (cf. DE-A 102 35 847). In this case, essentially water will be condensed out of the low boiler gas stream which then escapes at the top of the first condensation column, appropriately by direct cooling in a downstream space (second column) which is essentially free of internals (this space can also be integrated into the condensation column for the purpose of acid water formation; such a quench space free of internals is then normally separated from the uppermost separating internal within the condensation column, for example, by means of a chimney tray) or comprises internals by means of a quench liquid 2. The condensate obtained is in turn the acid water. A portion of the acid water will then advisably be recycled into it to increase the separating performance at the top of the first condensation column. A further portion of the acid water is cooled indirectly in an external heat exchanger and used as the quench liquid 2, and the acrylic acid can in turn be extracted in accordance with the invention from the remaining amount of acid water. Constituents of the low boiler stream which are more volatile than water in turn form residual gas which is normally recycled at least partly as cycle gas into the gas phase partial oxidation or used as stripping gas.

Appropriately, the dual-flow trays in the preferred variant of the process according to the invention extend in the condensation column up to about the cross section in the condensation column from which the acrylic acid contents of the reflux liquid viewed toward the top of the column are ≦90% by weight, based on the weight of the reflux liquid.

The number of dual-flow trays is, as already stated, generally from 25 to 45 for the preferred variant of the fractional condensation described. Their orifice ratio is appropriately from 12 to 25%. As passages, the dual-flow trays preferably have circular holes with a uniform circle diameter. The latter is appropriately from 10 to 20 mm. If required, the hole diameter in the condensation column can be narrowed or widened from the top downward and/or the number of holes can be reduced or increased (for example, the hole diameter can be a uniform 14 mm and the orifice ratio can increase from 17.4% to 18.3% from the top downward). However, the number of holes may also be constant over all dual-flow trays. In addition, the circular holes are preferably arranged uniformly in strict triangular pitch over the individual dual-flow trays (cf. DE-A 102 30219).

Moreover, the punching burr of the passage orifices punched out in the dual-flow trays preferably points downward in the condensation column (this reduces undesired polymer formation).

It is advisable in accordance with the invention when the number of dual-flow trays used in the condensation column corresponds to from about 10 to 15 theoretical plates.

The number of hydraulically sealed crossflow mass transfer trays which follows the dual-flow trays in the condensation column preferred in accordance with the invention will, as already mentioned, generally be from 30 to 50. Their orifice ratio will be appropriately from 5 to 25%, preferably from 10 to 20% (the orifice ratio quite generally represents the percentage of the passage cross sections in the total cross section; in the crossflow mass transfer trays to be used with preference, it is quite generally appropriately within the aforementioned range).

Preference is given in accordance with the invention to using single-flow crossflow mass transfer trays.

In general, the number of hydraulically sealed crossflow trays for the preferred variant of the fractional product gas mixture condensation will be such that it corresponds to from about 10 to 30, frequently 25, theoretical plates.

Both the hydraulically sealed crossflow trays and any valve trays used have at least one downcomer. They may both have either a single-flow or multiflow, for example two-flow, configuration. Even in the case of single-flow configuration, they may have more than one downcomer. In general, the feed shafts of the valve trays are also hydraulically sealed.

The polymerization inhibition of the quench system 1 for the product gas mixture of the partial gas phase oxidation can be accomplished either by means of polymerization inhibitors present in bottoms liquid (from the condensation column) used for quenching or by means of polymerization inhibitors present in high boiler fraction (from the condensation column) used for quenching.

Once again, the reason for the advantage of the process according to the invention is that it enables an increased yield of crude acrylic acid with essentially the same purity. All statements made in this document apply in particular to a product gas mixture which has been obtained by (preferably two-stage) heterogeneous partial oxidation of propylene to acrylic acid. The above-described preferred variant of the process according to the invention in no way restricts the general performability.

Finally, it should also be emphasized that both the first stripping gas and the second stripping gas advantageously comprise molecular oxygen.

In addition, it should also be added that, in the process according to the invention, if appropriate, another liquid absorbent (other than the reflux liquid) whose boiling point $T_s$ at a pressure of 1 atm is greater than or equal to the boiling point $T_w$ of water at a pressure of 1 atm is fed to the condensation column via a feed point disposed between its first side draw and its second side draw. In principle, it is possible to proceed, for example, as described in EP-A 1 818 324. Useful such absorbents may, for example, be relatively higher-boiling organic liquids. For example, those organic liquids recommended as absorbents in DE-A 103 36 386 and the prior art cited in this document are suitable. It will be appreciated that it is also possible to use the absorbents recommended in EP-A 1 818 324 at this point.

For example, suitable such absorbents are high-boiling (inert) liquid hydrophobic organic liquids, as detailed in EP-A 722 926, DE-A 44 36 243 and DE-A 103 36 386 (e.g. dimethyl phthalate, diethyl phthalate and/or Diphyl). These are, for example, liquids whose boiling point at standard pressure (1 atm) is above the boiling point of acrylic acid and which consist to an extent of at least 70% by weight of those molecules which do not comprise any external active polar group and are thus, for example, incapable of forming hydrogen bonds. Examples of such absorbents include mixtures of diphenyl ether (from 70 to 75% by weight) and diphenyl (from 25 to 30% by weight) referred to as Diphyl®, and the mixture of a mixture of from 70 to 75% by weight of diphenyl ether and from 25 to 30% by weight of diphenyl, and also, based on this mixture, from 0.1 to 25% by weight of dimethyl phthalate.

It will be appreciated that such absorbents used may also be aqueous liquids. For example, useful such aqueous liquids are those recommended in EP-A 1 818 324. Among others, water is included in these absorbents. It will be appreciated that such an aqueous absorbent used may also be the aqueous phase remaining in extracted form in the acid water extraction to be performed in accordance with the invention. Typically, the aforementioned absorbent addition will pursue the purpose of lowering, in a controlled manner, the proportion of particular secondary components present in the crude acrylic acid conducted out of the condensation column via the first side draw. It is therefore advantageous when the absorbent used itself comprises these secondary components in a very low proportion by weight at most (and preferably not at all).

In the case of use of an aqueous absorbent, it is, for example, favorable when its individual proportions by weight of secondary components are less than the corresponding proportions by weight in the acid water.

The supply of aqueous absorbents (for example of water) is suitable, inter alia, in a particularly advantageous manner for reducing the content of aldehydes having a boiling point comparable to acrylic acid (especially the content of furfurals) in the crude acrylic acid conducted out of the condensation column via the first side draw. In principle, such an absorbent used may also be a mixture of an aqueous liquid and of an organic liquid. In principle, such a mixture may also be polyphasic.

The absorbent may advantageously be conducted into the condensation column at the same height as the reflux liquid. Both may also be conducted into the condensation column in a mixture.

The temperature of the absorbent when supplied to the condensation column may vary over a wide range. It may be either above or below the temperature of the reflux liquid. Frequently, the temperature of the absorbent will be within the interval of ±20° C. around the temperature of the reflux liquid. The temperature of the reflux liquid and of the absorbent are preferably the same.

When the crude acrylic acid withdrawn via the first side draw comprises portions of the absorbent used additionally, they are generally removed therefrom by means of the crystallizative further purification of the crude acrylic acid described in this document. Otherwise, an absorbent used additionally is normally obtained in the bottoms liquid conducted out of the condensation column and can, after a removal therefrom in the manner described above, be reused as an absorbent.

Appropriately in accordance with the invention, the mass flow of an absorbent conducted into the condensation column, based on the mass flow of acrylic acid conducted into the condensation column as a constituent of the product gas mixture supplied to the condensation column, will be from 0 to 30%.

Based on the longitudinal section of the condensation column disposed between the first side draw and the second side draw from the column, the supply of an absorbent into the condensation column will, appropriately from an application point of view, be conducted into the upper third of this longitudinal section.

Instead of being applied to crude acrylic acid obtainable in accordance with the invention, the crystallizative further purification of crude acrylic acid described in this document can also be applied to crude acrylic acid obtainable by the procedure described in DE-A 103 36 386 (especially such a crystallizative further purification according to claims 16 to 20 of the present document). It will be appreciated that such a crystallizative further purification can also be applied to any desired mixture of the two aforementioned types of crude acrylic acid. Such a procedure will be used, for example, when the inventive removal process and a removal process according to DE-A 103 36 386 are operated in parallel in order to remove acrylic acid from product gas mixtures of heterogeneously catalyzed partial gas phase oxidations (if appropriate operated in parallel) of $C_3$ precursors of acrylic acid. In the case that the operation of the inventive fractional condensation for such an acrylic acid removal should temporarily be out of service, but crude acrylic acid obtained according to DE-A 103 36 386 were still to be fed to this crystallizative further purification, a partial stream (based on the mass flow of crude acrylic acid supplied to the crystallizative further purification, a mass flow of from 5 to 30%, typically from 10 to 20% (the crystals removed must remain on-spec); the remaining residual stream of mother liquor will normally be recycled into the crystallization (together (in a mixture) with the mass flow of crude acrylic acid)) of the mother liquor obtained in the removal of the suspension crystals from the acrylic acid crystal suspension would be stored intermediately in a storage tank (the supply to the storage tank may be continuous or in cycles) and, after the fractional condensation has been restarted, recycled gradually into the fractional condensation in a mixture with mother liquor which is then obtained in accordance with the invention (based on the mass flow which is then of mother liquor obtained in accordance with the invention and is recycled into the fractional condensation, in a mass flow of from >0 to 20%, preferably from >0 to 10%). For this purpose, the withdrawal from the storage tank may be continuous or in cycles. It is normally withdrawn such that the crystals obtained are on-spec (the design capacity of the crystallization is generally above the design capacity of the production of the crude acrylic acid; briefly, crystallizative further purification is, though, also possible above the design capacity of the crystallization).

The present invention thus comprises especially the following embodiments:

1. A process for preparing acrylic acid, in which a product gas mixture comprising acrylic acid, steam and secondary components is obtained by heterogeneously catalyzed gas phase partial oxidation of at least one $C_3$ precursor of acrylic acid with molecular oxygen over solid-state catalysts at elevated temperature, the temperature of the product gas mixture comprising acrylic acid, steam and secondary components is, if appropriate, reduced by direct and/or indirect cooling, and the product gas mixture comprising acrylic acid, steam and secondary components is then passed into a condensation column equipped with separating internals, allowed to ascend into itself within the condensation column and thus fractionally condensed, and crude acrylic acid comprising water and secondary components depleted overall is conducted as the target product out of the condensation column via a first side draw disposed above the feed point of the product gas mixture into the condensation column, as are acid water still comprising acrylic acid and secondary components via a second liquid phase draw (preferably a side draw) disposed above the first side draw and a residual gas mixture comprising secondary components having lower boiling points than water at the top of the condensation column and a bottoms liquid still comprising acrylic acid and conversion products and secondary components having higher boiling points than acrylic acid from the bottom space of the condensation column, a portion of the acid water withdrawn is recycled as such and/or after cooling thereof as reflux liquid into the condensation column and the crude acrylic acid is subjected if appropriate to at least one further thermal separation process for the purpose of its further purification, wherein acrylic acid present at least in a portion of acid water not recycled into the condensation column is taken up from the acid water into an organic solvent by extraction with the organic solvent to form an organic extract comprising acrylic acid, then the acrylic acid is removed from the organic extract using at least one thermal separation process and acrylic acid removed from the extract is recycled into the condensation column or sent to the further purification of the crude acrylic acid and/or taken up into the aqueous solution of a metal hydroxide.

2. A process according to claim 1, wherein the $C_3$ precursor is propylene or acrolein or a mixture of propylene and acrolein.

3. A process according to embodiment 1 or 2, wherein acrylic acid present at least in 25% by weight of acid water not recycled into the condensation column is taken up from the acid water into an organic solvent by extraction with the organic solvent to form an organic extract comprising acrylic acid, then the acrylic acid is removed from the organic extract using at least one thermal separation process and acrylic acid removed from the extract is recycled into the condensation column or sent to the further purification of the crude acrylic acid and/or taken up into the aqueous solution of a metal hydroxide.

4. A process according to any of embodiments 1 to 3, wherein the extraction of the acrylic acid from the acid water is performed in an extraction column which comprises structured packings and/or sieve trays as separating internals.

5. A process according to embodiment 4, wherein the organic solvent is introduced at the top of the extraction column and the acid water in the bottom region of the extraction column, and the organic solvent ascends as a dispersed phase in the continuous acid water phase, or wherein the acid water is introduced at the top of the extraction column and the organic solvent in the bottom region of the extraction column, and the organic solvent ascends as a dispersed phase in the continuous acid water phase.

6. A process according to any of embodiments 1 to 5, wherein the organic solvent comprises at least one ester of an aliphatic or aromatic monocarboxylic acid comprising from 5 to 20 carbon atoms and an alcohol having from 1 to 8 carbon atoms.

7. A process according to any of embodiments 1 to 5, wherein the organic solvent comprises at least one diester of an aliphatic or aromatic dicarboxylic acid comprising from 5 to 20 carbon atoms and an alcohol having from 1 to 8 carbon atoms.

8. A process according to any of embodiments 1 to 5 or according to embodiment 7, wherein the organic solvent is dimethyl phthalate, diethyl phthalate, dimethyl isophthalate, diethyl isophthalate, dimethyl terephthalate and/or diethyl terephthalate.

9. A process according to any of embodiments 1 to 8, wherein the boiling point of the organic solvent at atmospheric pressure is $\geqq 200°$ C.

10. A process according to any of embodiments 1 to 9, wherein the acrylic acid is removed from the organic extract by stripping with a first stripping gas and the acrylic acid-laden first stripping gas is recycled into the condensation column and/or the acrylic acid present in the first laden stripping gas is taken up into the aqueous solution of a metal hydroxide.

11. A process according to any of embodiments 1 to 9, wherein the acrylic acid is removed from the organic extract by stripping with a first stripping gas and the resulting acrylic acid-laden first stripping gas is used as the second stripping gas in order to strip the bottoms liquid conducted out of the condensation column free of acrylic acid still present and the resulting acrylic acid-laden second stripping gas is recycled into the condensation column and/or the acrylic acid present in the second stripping gas is taken up into the aqueous solution of a metal hydroxide.

12. A process according to embodiment 11, wherein the stripping of the bottoms liquid conducted out of the condensation column is performed in a stripping column provided with separating internals, and the temperature in the bottom of the stripping column is from 150 to 190° C.

13. A process according to embodiment 11 or 12, wherein the acrylic acid-laden second stripping gas is subjected to a countercurrent rectification before it is recycled into the condensation column laden with acrylic acid and/or the acrylic acid present therein is taken up into the aqueous solution of a metal hydroxide.

14. A process according to any of embodiments 10 to 13, wherein the first stripping gas used is air, $N_2$, $CO_2$ and/or steam.

15. A process according to any of embodiments 10 to 13, wherein the first stripping gas used is residual gas mixture.

16. A process according to any of embodiments 1 to 15, wherein the crude acrylic acid is purified further by crystallization.

17. A process according to embodiment 16, wherein a portion of the acid water not recycled into the condensation column is added to the crude acrylic acid before the crystallizative further purification.

18. A process according to embodiment 16 or 17, wherein the crystallizative further purification of the crude acrylic acid or the mixture thereof with acid water is effected by suspension crystallization.
19. A process according to embodiment 18, wherein a wash column is used additionally to separate mother liquor remaining in the suspension crystallization and suspension crystals formed.
20. A process according to any of embodiments 17 to 19, which is followed by a process for free-radical polymerization in which molten acrylic acid crystals and/or the metal salt thereof is polymerized.
21. A process according to any of embodiments 10, 11, 13, which is followed by a process for free-radical polymerization in which acrylic acid taken up from laden first and/or second stripping gas into the aqueous solution of a metal hydroxide is polymerized.
22. A process according to any of embodiments 1 to 21, wherein a portion of the residual gas mixture is recycled as cycle gas into the gas phase partial oxidation.
23. A process according to any of embodiments 1 to 22, wherein the organic solvent has a mass density which, under the conditions of the extraction, differs from that of water by $\geq 25$ kg/m$^3$.
24. A process according to any of embodiments 1 to 23, wherein the aqueous solution of a metal hydroxide comprises NaOH, KOH, Ca(OH)$_2$ and/or Mg(OH)$_2$ in dissolved form.
25. A process according to any of embodiments 1 to 24, wherein a liquid absorbent whose boiling point $T_s$ at a pressure of 1 atm is greater than or equal to the boiling point $T_w$ of water at a pressure of 1 atm is fed to the condensation column via a feed point disposed between its first side draw and its second side draw.

U.S. Provisional Patent Application No. 60/886,771, filed Jan. 26, 2007, and No. 60/988,619, filed Nov. 16, 2007, are incorporated into the present patent application by literature reference. With regard to the abovementioned teachings, numerous changes and deviations from the present invention are possible. It can therefore be assumed that the invention, within the scope of the appended claims, can be performed differently from the way described specifically herein.

EXAMPLES AND COMPARATIVE EXAMPLE

Example 1 (A Steady State is Described)

A two-stage heterogeneously catalyzed gas phase partial oxidation of propylene of chemical-grade purity in three parallel tandem reactor lines affords a product gas mixture which has a temperature of 270° C. and a pressure of 1.5 bar and the following composition:

| | |
|---|---|
| 10.3141% by wt. of | acrylic acid, |
| 0.2609% by wt. of | acetic acid, |
| 4.6513% by wt. of | water, |
| 0.0251% by wt. of | formic acid, |
| 0.0851% by wt. of | formaldehyde, |
| 0.1052% by wt. of | acrolein, |
| 0.0024% by wt. of | propionic acid, |
| 0.0028% by wt. of | furfurals, |
| 0.0012% by wt. of | allyl acrylate, |
| 0.0013% by wt. of | allyl formate, |
| 0.0032% by wt. of | benzaldehyde, |
| 0.1151% by wt. of | maleic anhydride, |
| 0.0096% by wt. of | benzoic acid, |

-continued

| | |
|---|---|
| 0.0126% by wt. of | phthalic anhydride, |
| 2.0334% by wt. of | CO$_2$, |
| 0.6604% by wt. of | CO, |
| 0.6259% by wt. of | propane, |
| 0.1459% by wt. of | propylene, |
| 2.3772% by wt. of | O$_2$, and |
| 78.5670% by wt. of | N$_2$. |

The reaction gas mixture to be fed in each case to the three tandem reactor lines is in each case a mixture of cycle gas and chemical-grade propylene, into which primary air is subsequently also metered. The mixing is accomplished in each case by a static mixer.

Between the first-stage reactor and the second-stage reactor, secondary air is also fed in each case.

The quantitative ratios are adjusted to the operating state of the particular reactor line and are, upstream of the first reactor:
A) Cycle gas=25 339 kg/h, Chemical-grade propylene=3481 kg/h, Air=17 791 kg/h.
B) Cycle gas=38 341 kg/h, Chemical-grade propylene=4035 kg/h, Air=19 561 kg/h.
C) Cycle gas=30 874 kg/h, Chemical-grade propylene=4689 kg/h, Air=23 936 kg/h.

The significant contents of the three resulting reaction gas mixture streams are:

| | | |
|---|---|---|
| A) | 10.2909% by wt. of | O$_2$, |
| | 1.2926% by wt. of | CO$_2$, |
| | 0.4136% by wt. of | CO, |
| | 0.6533% by wt. of | propane, |
| | 7.2976% by wt. of | propylene, |
| | 1.5383% by wt. of | H$_2$O, and |
| | 78.2693% by wt. of | N$_2$; |
| B) | 8.9782% by wt. of | O$_2$, |
| | 1.4660% by wt. of | CO$_2$, |
| | 0.4710% by wt. of | CO, |
| | 0.6744% by wt. of | propane, |
| | 6.3907% by wt. of | propylene, |
| | 1.6626% by wt. of | H$_2$O, and |
| | 80.0789% by wt. of | N$_2$; |
| and | | |
| C) | 10.6981% by wt. of | O$_2$, |
| | 1.2357% by wt. of | CO$_2$, |
| | 0.3948% by wt. of | CO, |
| | 0.6500% by wt. of | propane, |
| | 7.6922% by wt. of | propylene, |
| | 1.4968% by wt. of | H$_2$O, and |
| | 77.5992% by wt. of | N$_2$. |

The product gas mixture (177 184 kg/h) is cooled in a spray cooler (quench 1) operated in cocurrent by direct cooling to a temperature of 107.3° C.

The liquid to be used for the direct cooling of the product gas mixture (quench liquid 1) is a portion of a mixture 1 of bottoms liquid which is withdrawn from the bottom of the condensation column described below, and a small amount (251 kg/h) of condensate withdrawn from the quench circuit 0.

Contents of this mixture 1 (temperature=104.9° C.) are:

| | |
|---|---|
| 64.6170% by wt. of | acrylic acid, |
| 0.3883% by wt. of | acetic acid, |
| 1.0300% by wt. of | water, |

-continued

| | |
|---|---|
| 0.0132% by wt. of | formic acid, |
| 0.0011% by wt. of | formaldehyde, |
| 0.0083% by wt. of | acrolein, |
| 0.0384% by wt. of | propionic acid, |
| 0.3331% by wt. of | furfurals, |
| 0.0016% by wt. of | allyl acrylate, |
| 0.0008% by wt. of | allyl formate |
| 0.1609% by wt. of | benzaldehyde, |
| 4.4001% by wt. of | maleic anhydride, |
| 0.3976% by wt. of | benzoic acid, |
| 0.5228% by wt. of | phthalic anhydride, |
| 12.8970% by wt. of | diacrylic acid, ⎫ Michael adducts, |
| 13.9178% by wt. of | polyacrylic acid ⎭ |
| 0.1258% by wt. of | phenothiazine, |
| 0.4408% by wt. of | MEHQ, |
| 0.7052% by wt. of | other high-boiling constituents, and |
| 0.0002% by wt. of | oxygen. |

Only an amount of 458 m³/h is fed with the aforementioned temperature to the spray cooler of the quench circuit 1 for the direct cooling of the product gas mixture. 3137 kg/h are supplied as feed to the second stripping column and 1195 kg/h are fed to the quench circuit 0 in order thus to inhibit the quench liquid 0 and the reflux liquid to be conducted to the uppermost tray of the second stripping column against undesired polymerization.

The mixture of product gas mixture cooled to 107.3° C. and unevaporated quench liquid 1 which results in the direct cooling is conducted as such into the bottom of the condensation column. The pressure in the bottom space and in the quench 1 is 1.50 bar.

The internal diameter of the condensation column in the region of the Thromann trays is 6.5 m and otherwise 6.0 m.

3137 kg/h of the mixture 1 are supplied as feed to the second stripping column which comprises 50 dual-flow trays as separating internals. Just like the condensation column, the second stripping column is insulated thermally from the environment. The internal diameter of the second stripping column over all dual-flow trays is a uniform 2.4 m. The dual-flow trays are arranged equidistantly (400 mm) in the second stripping column. Their orifice ratio is a uniform 12%. Viewed from the bottom upward, the hole diameter of the first eight dual-flow trays is a uniform 14 mm (hole diameter corresponding to strict triangular pitch; distance of hole center to hole center equals 26 mm), and the hole diameter of all subsequent dual-flow trays is a uniform 14 mm (hole arrangement likewise corresponding to strict triangular pitch; distance from hole center to hole center equals 25 mm).

The 3137 kg/h of the mixture 1 are supplied with a temperature of 105.2° C. to the eighth dual-flow tray (from the bottom).

The energy is supplied into the second stripping column by means of an external forced-circulation three-flow tube bundle flash evaporator (cf. Grundoperationen chemischer Verfahrenstechnik, 4th edition, Steinkopff Verlag Dresden, 1974, p. 434). 271 650 kg/h of bottoms liquid which have been withdrawn from the bottom of the second stripping column and have a temperature of 151.7° C. and a pressure of 1.655 bar are fed thereto, and have the following contents:

| | |
|---|---|
| 2.0713% by wt. of | acrylic acid, |
| 0.2201% by wt. of | acetic acid, |
| 0.2608% by wt. of | water, |
| 0.0094% by wt. of | formic acid, |
| 0.0001% by wt. of | formaldehyde, |

-continued

| | |
|---|---|
| 0.0036% by wt. of | acrolein, |
| 0.0017% by wt. of | propionic acid, |
| 0.0001% by wt. of | furfurals, |
| 0.0008% by wt. of | allyl formate, |
| 0.5731% by wt. of | diethyl phthalate, |
| 0.7638% by wt. of | benzaldehyde, |
| 23.2670% by wt. of | maleic anhydride, |
| 2.2693% by wt. of | benzoic acid, |
| 2.9848% by wt. of | phthalic anhydride, |
| 38.3947% by wt. of | diacrylic acid ⎫ Michael adducts, |
| 21.2842% by wt. of | polyacrylic acid ⎭ |
| 0.7185% by wt. of | phenothiazine |
| 2.5151% by wt. of | MEHQ, |
| 4.6615% by wt. of | other high-boiling constituents, and |
| 0.0001% by wt. of | oxygen. |

The heat carrier conducted through the space surrounding the heat exchanger tubes (in a meandering manner, conducted by appropriate deflecting plate) is steam (pressure=16 bar). As it flows through the heat exchanger tubes, the bottoms liquid is heated, and 270 900 kg/h of the total amount conducted through the heat exchanger are recycled with a temperature of 158.6° C. into the bottom of the second stripping column. 750 kg/h of the total amount of bottoms liquid conducted through the heat exchanger are branched off, degassed and, diluted with methanol, sent to residue incineration.

In addition, 17 424 kg/h of first laden gas conducted out of the first stripping column at the top thereof are fed into the bottom of the second stripping column with a temperature of 82.2° C. and a pressure of approx. 2.50 bar, and have the following contents:

| | |
|---|---|
| 3.3977% by wt. of | acrylic acid, |
| 1.1198% by wt. of | acetic acid, |
| 4.1030% by wt. of | water, |
| 0.0622% by wt. of | formic acid, |
| 0.0321% by wt. of | formaldehyde, |
| 0.1181% by wt. of | acrolein, |
| 0.0030% by wt. of | propionic acid, |
| 0.0006% by wt. of | furfurals, |
| 0.0139% by wt. of | allyl formate, |
| 0.0247% by wt. of | diethyl phthalate, |
| 2.5667% by wt. of | $O_2$, |
| 2.1951% by wt. of | $CO_2$, |
| 0.7129% by wt. of | CO, |
| 0.6756% by wt. of | propane, |
| 0.1575% by wt. of | propylene, and |
| 84.8133% by wt. of | $N_2$. |

Second laden gas is conducted out of the top of the second stripping column in an amount of 25 831 kg/h (temperature=96.7° C., pressure=1.58 bar) and cooled to a temperature of 80.9° C. by direct cooling in a spray cooler operated in countercurrent (quench 0) and partially condensed.

The gas mixture remaining in the direct cooling is recycled into the bottom space of the condensation column (not immersed) with a pressure of 1.58 bar in an amount of 20 755 kg/h and with the following contents:

| | |
|---|---|
| 18.5793% by wt. of | acrylic acid, |
| 0.9849% by wt. of | acetic acid, |
| 3.6185% by wt. of | water, |
| 0.0571% by wt. of | formic acid, |
| 0.0271% by wt. of | formaldehyde, |

|  |  |
|---|---|
| 0.1006% by wt. of | acrolein, |
| 0.0099% by wt. of | propionic acid, |
| 0.0436% by wt. of | furfurals, |
| 0.0003% by wt. of | allyl acrylate, |
| 0.0117% by wt. of | allyl formate, |
| 0.0053% by wt. of | benzaldeyde, |
| 0.0642% by wt. of | maleic anhydride |
| 0.0001% by wt. of | benzoic acid, |
| 0.0001% by wt. of | diacrylic acid, |
| 0.0001% by wt. of | MEHQ, |
| 2.1548% by wt. of | $O_2$, |
| 1.8428% by wt. of | $CO_2$, |
| 0.5985% by wt. of | CO, |
| 0.5672% by wt. of | propane, |
| 0.1322% by wt. of | propylene, and |
| 71.2018% by wt. of | $N_2$. |

The quench liquid 0 used is 32 956 kg/h of a mixture of 1195 kg/h of mixture 1 and 37 761 kg/h of condensate formed in the direct cooling in the quench 0 (to this end, this portion of the mixture is cooled from 80.9° C. to 40.1° C. in an indirect heat exchanger (type: spiral heat exchanger; against water)). 6020 kg/h of this mixture which has a temperature of 80.9° C. is conducted as reflux liquid to the uppermost tray of the second stripping column.

The mixture has the following contents:

|  |  |
|---|---|
| 87.9166% by wt. of | acrylic acid, |
| 2.3313% by wt. of | acetic acid, |
| 2.6130% by wt. of | $H_2O$, |
| 0.0688% by wt. of | formic acid, |
| 0.0010% by wt. of | formaldehyde, |
| 0.0151% by wt. of | acrolein, |
| 0.0480% by wt. of | propionic acid, |
| 0.2980% by wt. of | furfurals, |
| 0.0008% by wt. of | allyl acrylate, |
| 0.0096% by wt. of | allyl formate, |
| 0.0568% by wt. of | benzaldehyde, |
| 1.1099% by wt. of | maleic anhydride, |
| 0.0761% by wt. of | benzoic acid, |
| 0.1000% by wt. of | phthalic anhydride, |
| 2.4592% by wt. of | diacrylic acid ⎫ Michael adducts |
| 2.6522% by wt. of | polyacrylic acid ⎭ |
| 0.0240% by wt. of | phenothiazine, |
| 0.0847% by wt. of | MEHQ, |
| 0.1345% by wt. of | other high-boiling constituents, and |
| 0.0004% by wt. of | oxygen. |

A centrifugal droplet separator which prevents droplets of the bottoms liquid from being entrained upward out of the bottom space is integrated into the bottom space of the condensation column.

The bottom space of the condensation column is, as already mentioned, concluded at a column height (like all heights, calculated from the column bottom) of 7.80 m by a first collecting tray (chimney tray with about 16 uniformly distributed roofed chimneys; chimney diameter: 600 mm; chimney height: 1 m).

The collecting tray has a double-wall configuration with a 2° inward gradient and a central draw cup and draw nozzle (DN ~200). The free gas cross section is approx. 30%.

88 579 kg/h of high boiler fraction are conducted from this first collecting tray into the bottom space disposed below the first collecting tray.

The high boiler fraction has, at a temperature of 99.8° C. and a pressure of approx. 1.50 bar, the following contents:

|  |  |
|---|---|
| 94.6665% by wt. of | acrylic acid, |
| 0.5402% by wt. of | acetic acid, |
| 1.3577% by wt. of | water, |
| 0.0160% by wt. of | formic acid, |
| 0.0014% by wt. of | formaldehyde, |
| 0.0071% by wt. of | acrolein, |
| 0.0577% by wt. of | propionic acid, |
| 0.3814% by wt. of | furfurals, |
| 0.0023% by wt. of | allyl acrylate, |
| 0.0010% by wt. of | allyl formate, |
| 0.1279% by wt. of | benzaldehyde, |
| 2.1925% by wt. of | maleic anhydride, |
| 0.0051% by wt. of | benzoic acid, |
| 0.0046% by wt. of | phthalic anhydride, |
| 0.6008% by wt. of | diacrylic acid, |
| 0.0061% by wt. of | phenothiazine |
| 0.0314% by wt. of | MEHQ, and |
| 0.0002% by wt. of | $O_2$. |

The bottom temperature is 104.9° C. and the bottom pressure (at the liquid level) is 1.51 bar.

2.0 m above the first collecting tray is disposed the first of initially 15 dual-flow trays. These dual-flow trays (number of holes a uniform 33 678) are mounted equidistantly with a tray separation of 380 mm. The passage orifices consist of circular orifices of a uniform diameter of 14 mm, the punching burr pointing downward in the separating column. The arrangement of the centers of the passage circles follows strict triangular pitch. The closest separation of two circle centers is 24.5 mm.

The fifteenth dual-flow tray functions as a distributor tray. For this purpose, the column wall comprises, between the second collecting tray and the fifteenth dual-flow tray, two inserted tubes (DN ~150) with 45 drain bores (diameter: 15 mm) per inserted tube.

Crude acrylic acid and mother liquor are recycled via the inserted tubes into the condensation column.

The first series of dual-flow trays is concluded with a second collecting tray (chimney tray with 16 approximately uniformly distributed roofed chimneys; chimney height approx. 1.70 m, central draw cup with draw nozzle (DN ~250), free gas cross section of 30%), which is mounted 1.50 m above the last dual-flow tray.

From this second collecting tray, crude acrylic acid with a temperature of 97.1° C. is withdrawn continuously at 1.48 bar as the first side draw, and has the following contents:

|  |  |
|---|---|
| 96.7716% by wt. of | acrylic acid, |
| 0.8253% by wt. of | acetic acid, |
| 1.6640% by wt. of | water, |
| 0.0213% by wt. of | formic acid, |
| 0.0018% by wt. of | formaldehyde, |
| 0.0070% by wt. of | acrolein, |
| 0.0681% by wt. of | propionic acid |
| 0.1642% by wt. of | furfurals, |
| 0.0027% by wt. of | allyl acrylate, |
| 0.0012% by wt. of | allyl formate, |
| 0.0164% by wt. of | benzaldehyde, |
| 0.1052% by wt. of | maleic anhydride, |
| 0.3278% by wt. of | diacrylic acid, |
| 0.0050% by wt. of | phenothiazine, |
| 0.0180% by wt. of | MEHQ, and |
| 0.0002% by wt. of | oxygen. |

18 474 kg/h of the crude acrylic acid withdrawn from the second collecting tray, together with mother liquor which has been obtained in the crystallizative further purification of withdrawn crude acrylic acid and has been heated to 90° C. in the indirect heat exchange with drawn crude acrylic acid and steam as a heat carrier (72 716 kg/h), are recycled into the condensation column via aforementioned inserted tubes immediately below the second collecting tray to the dual-flow tray which follows below the second collecting tray.

89 303 kg/h of the crude acrylic acid withdrawn from the second collecting tray are cooled to a temperature of 29° C. by multistage indirect heat exchange (inter alia, in a thermally integrated manner against aforementioned mother liquor to be recycled into the condensation column), and if appropriate intermediately buffered in a tank farm. 1204 kg/h of acid water withdrawn from the second side draw of the condensation column are then added to the cooled crude acrylic acid.

The acid water has the following contents:

| | |
|---|---|
| 10.7677% by wt. of | acrylic acid, |
| 6.4390% by wt. of | acetic acid, |
| 79.5610% by wt. of | water, |
| 0.7038% by wt. of | formic acid, |
| 2.4712% by wt. of | formaldehyde, |
| 0.0132% by wt. of | acrolein, |
| 0.0082% by wt. of | propionic acid, |
| 0.0013% by wt. of | furfurals, |
| 0.0331% by wt. of | allyl formate, |
| 0.0001% by wt. of | MEHQ, and |
| 0.0013% by wt. of | oxygen. |

The resulting mixture is cooled to 16° C. by another indirect heat exchange (against cooling brine (water/glycol mixture; 25-35% by weight of glycol and 65-75% by weight of water)) and then conducted into two to three cooling-disk crystallizers operated in parallel (cf. WO 2006/111565) in distribution. Each of these comprises a trough in which 24 wiped circular cooling plates (each of which is flowed through internally by a cooling medium (mixture of water and glycol; glycol content=25 to 35% by weight)) are arranged hanging in succession at an equidistant separation of 30±1 cm (plate diameter=3.3 m). The particular cooling medium is passed on, in countercurrent to the crystallizing mixture through the particular crystallizer, from cooling disk to the cooling disk after next. In other words, the particular cooling medium is conducted with division in the form of two parallel streams through the cooling plates of the particular crystallizer. One stream leads through the even-numbered cooling plates, the other stream through the odd-numbered inserted cooling plates (numbering of the cooling disks in flow direction beginning with 1). The particular amount of cooling medium per crystallizer is a total of 180-220 t/h (metric tons), i.e. 90-110 t/h per stream. The pressure drop per cooling disk is from 60 to 100 mbar. The entrance temperature of the cooling medium (of the brine) is from +2.5 to +3° C. The exit temperature is 2.5° C. higher. The wall thickness of the cooling surfaces manufactured from stainless steel is 4 mm. The heat transfer coefficient on the brine side is from about 1500 to 2500 W/(m²·K). The heat transfer coefficients are usually from 380 to 420 W/(m²·K). The specific cooling performance is 1.5±0.2 kW/m² of cooling surface. The wiping of the cooling plates suppresses the formation of a crystal layer. The crude acrylic acid of increased water content is conducted continuously from the back forward through the particular crystallizer (pumped or under overflow control). At the same time, the monophasic crude acrylic acid of increased water content thickens (residence time 2.5 h) to a biphasic suspension comprising acrylic acid crystals as a solid phase having a temperature of from 7 to 8.5° C. and a solids content at the outlet of about 25% by weight. The mass density of the suspension is typically from 1110 to 1115 kg/m³. The speed of the wipers is from 5 to 6 revolutions per minute. The shaft which drives the wipers and passes through the centers of the cooling disks is sealed with water-washed stuffing box packings (packing threads of Teflon or graphite, wash rate=a few liters per hour up to several 10s of l/h per seal.

On the circumference of the cooling disks, where it is not possible to wipe, a hollow profile (e.g. a tube in the simplest embodiment) is mounted (for example welded on), and is heated by means of a second heat carrier (for example likewise water/glycol mixture) (to a temperature above the crystallization temperature; usually from the temperature range from 8 to 20° C., preferably from 10 to 14° C.). These peripheral heaters are flowed through in parallel by the second heat carrier.

In addition, the wipers are preferably segmented in radial direction (4 segments). The specific pressing force of the wipers in the installed state, perpendicular to the cooling surface, is from 3 to 5 N per cm of active wiper edge length. The wiper material used is high molecular weight polyethylene or ultra-high molecular weight polyethylene, for example Multilene® PE 1000. In addition to the wipers, the shaft drives paddles (there are appropriately two each in a symmetrical arrangement between two cooling disks and before the first and last cooling disk), which bring about improved mixing.

In the last section of the particular crystallizer in conveying direction of the suspension (preferably beyond the last cooling disk), the suspension is conducted through an attached tube (appropriately mounted immersed; alternatively, the suspension can flow over an overflow weir into a stirred collecting vessel from which the wash columns are charged) to hydraulic melt wash columns, as described in EP-A 1 272 453, EP-A 1 448 283, WO 03/041833, EP-A 1 305 097, DE-A 101 56 016, DE-A 10 2005 018 702 and in DE-A 102 23 058, in order to remove the mother liquor from the suspension crystals. The wash column diameter is 1.4 m. The wash columns are charged with crystal suspension by means of a centrifugal pump (channel wheel type), the flow preferably being controlled by means of speed regulation of the pump. The control stream pump is likewise configured as a centrifugal pump with regulating valve. Typically, the control stream flow employed to regulate a wash column is from 5 to 60 t/h, usually from 8 to 30 t/h. In some cases, it is possible to operate the particular wash column without a control stream when the amount of liquid supplied with the suspension is already sufficient for the transport of the crystal bed. Typical ratios of effective transport pressure difference to effective wash pressure difference are from 1.1 to 3, usually from 1.2 to 1.8. The blade speed is usually at values of from 5 to 10 per minute. The temperature in the melt circuit is normally from 13 to 16° C. The monitoring of the filtration front is undertaken in accordance with DE-A 10 2005 018 702 by means of two pressure drop measurements over different bed lengths placed in a ratio relative to one another. The wash front is controlled by means of temperature measurement in the crystal bed.

For control reasons, the total height of the crystal bed is from 250 to 1500 mm, usually from 600 to 1100 mm. The wash front is typically from 100 to 200 mm above the blade. Suitable melt circuit pumps are centrifugal pumps with product-side flushing of the shaft seal (slip-ring seal; double design, with barrier medium cooled to 15-30° C. (water/glycol mixture)) or a magnet-coupled pump with increased flushing of the slide bearing. The circulation rate in the particular melt circuit is from 10 to 15 m³/h per tonne of purified crystals scrapped off with the blade. The melt circuit is stabilized according to the subsequent use in a column-specific manner with from 200 to 300 ppm by weight of MEHQ, or with from 40 to 70 ppm by weight of MEHQ, or with from 100 to 300 ppm by weight of PTZ. In addition, air is introduced into the melt circuit, or lean air (nitrogen-air mixture with ≦6% by volume of oxygen), whose excess (=proportion not dissolved in the wash melt) is removed by means of a gas separator before entry of the wash melt into the wash column. This establishes a content of dissolved oxygen of from 5 to 40 ppm by weight in the molten pure product.

[a] To prepare esterification-grade acrylic acid, it is sufficient to perform the removal of the suspension crystals by means of a centrifuge (for example a two- or three-stage pusher centrifuge) instead of in a melt wash column. Suitable screen gap sizes are from 150 to 300 μm; useable centrifugal accelerations are from 500 to 900 g, usually from 600 to 800 g; suitable stroke rates are from 40 to 80 strokes/min.

The crystals removed at the 2nd or 3rd stage of the centrifuge are preferably washed with from 0.15 to 0.3 kg of wash liquid per kg of crystals. The temperature of the wash liquid is from 15 to 30° C., preferably from 20 to 30° C. To avoid deposits, the solids discharge chute of the centrifuge is flushed with flushing liquid of temperature adjusted to from 15 to 30° C. Flush liquid and wash liquid are preferably molten crystals which have been removed and washed by means of the centrifuge. To prevent deposits and encrustations, it is appropriate to keep the centrifuge casing, the suspension feed tube and the wash liquid feed tube at a temperature of ≧15° C. and ≦40° C. The product space of the centrifuge is appropriately inertized with nitrogen or with a mixture of air and nitrogen. The shaft seal is purged with gas (for example nitrogen or a mixture of air and nitrogen) or with water.

b) Alternatively to the suspension crystallization, it is also possible to employ a layer crystallization (for example falling-film crystallization according to EP-A 616 998 or tube with complete flow-through) with 2 or 3 or more (for example from 2 to 4) purification stages. Instead of recycling the mother liquor of a next purification stage into a preceding purification stage, it can also be recycled together into the condensation column.]

17 894 kg/h of glacial acrylic acid (temperature=14° C., pressure=1.5 bar) are withdrawn from the melt circuits, which are stabilized by the addition of a total of 104 kg/h of a solution (temperature=25° C., pressure=1.1 bar) of 3 kg/h of MEHQ in 101 kg/h of glacial acrylic acid (25° C.) withdrawn from the melt circuits, and have the following contents:

| | | |
|---|---|---|
| 99.7334% | by wt. of | acrylic acid, |
| 0.2091% | by wt. of | acetic acid, |
| 0.0180% | by wt. of | water, |
| 0.0230% | by wt. of | propionic acid, |
| 0.0001% | by wt. of | furfurals, |
| <0.0001% | by wt. of | benzaldehyde, |
| 0.0001% | by wt. of | maleic anhydride, |
| 0.0002% | by wt. of | diacrylic acid, |
| 0.0150% | by wt. of | MEHQ, and |
| 0.001% | by wt. of | $O_2$. |

It is outstandingly suitable for preparing superabsorbents based on poly-sodium acrylate.

5 kg/h of PTZ are dissolved in 352 kg/h of the aforementioned heated glacial acrylic acid to prepare an inhibitor solution 1 at 25° C. 19 kg/h of MEHQ are dissolved in 30 kg/h of inhibitor solution 1 to form inhibitor solution 2 which is likewise at 25° C.

17 439 kg/h of MEHQ-stabilized glacial acrylic acid (25° C., 1.5 bar) are fed to continuously to the storage tank.

The mother liquor removed in the wash columns is initially conducted into a heatable collecting vessel and from there into a tank. From this tank, it is (as already mentioned) heated to 90° C. with thermal integration and recycled in an amount of 72 716 kg/h, together with 18 474 kg/h of crude acrylic acid withdrawn at the second collecting tray, to the fifteenth dual-flow tray of the condensation column (counted from the bottom). The composition of this recycled mother liquor is as follows:

| | | |
|---|---|---|
| 94.6188% | by wt. of | acrylic acid, |
| 1.0690% | by wt. of | acetic acid, |
| 3.3562% | by wt. of | water, |
| 0.0378% | by wt. of | formic acid, |
| 0.0431% | by wt. of | formaldehyde, |
| 0.0088% | by wt. of | acrolein, |
| 0.0782% | by wt. of | propionic acid, |
| 0.2016% | by wt. of | furfurals, |
| 0.0034% | by wt. of | allyl acrylate, |
| 0.0021% | by wt. of | allyl formate, |
| 0.0202% | by wt. of | benzaldehyde, |
| 0.1292% | by wt. of | maleic anhydride, |
| 0.4025% | by wt. of | diacrylic acid, |
| 0.0061% | by wt. of | phenothiazine, |
| 0.0227% | by wt. of | MEHQ, and |
| 0.0003% | by wt. of | oxygen. |

2.9 m above the second collecting tray in the condensation column is disposed the first of 21 further dual-flow trays of the type already described (hole diameter again a uniform 14 mm, but number of holes a uniform 32 020, closest distance of two passage circle centers=24.5 mm), which are again arranged equidistantly with a tray separation of 380 mm.

800 mm above the last dual-flow tray, the condensation column begins to widen conically. 500 mm above the last dual-flow tray, this widening ends at a column diameter of 6.50 m.

At this height, i.e. 1.50 m above the last dual-flow tray, begins an equidistant (tray separation=500 mm) arrangement of 28 conventional, single-flow Thormann trays. The first of the Thormann trays from the bottom is one in which the liquid draining from the tray drains via six downcomers configured as tubes. These tubes are sealed hydraulically from the gas space of the next dual-flow tray down. The weir height of the six drain tubes decreases in flow direction of the crossflow tray. The hydraulic sealing has emptying orifices with impingement plates. The drain tubes are distributed uniformly in the last third of the tray cross section (opposite the feed onto the tray). The hydraulic sealing is effected into a cup with oblique overflow weir (45°).

Otherwise, the Thormann trays are configured such that a mutually opposite flow direction of the liquid is obtained in successive channels in flow direction through the arrangement of the motive slots in the hoods of the Thormann trays.

The orifice ratio of the Thormann trays is 14%. The ratio of chimney area to slot exit area is 0.8. The chimney height and the height of the drain weir is 40 mm. The tray clearance of the bubble-cap (distance between lower edge of slot and tray) is 10 mm. The slot height is 15 mm. The angle between obliquely angled slot and longitudinal edge of the hood is 30 degrees. The length of the longitudinal edge of the hood is a maximum of 800 mm. In the edge region of the column, the hood length is reduced down to 200 mm for reasons of adjustment to the roundness of the column. The distance between two hoods on one line in crossflow direction is 66 mm. The drain area of the downcomer is 1.5% based on the cross-sectional area of the tray. The width between the two lower longitudinal edges of a hood is 64 mm.

At the height of the uppermost Thormann tray, the separating column begins to narrow conically again. 700 mm above the uppermost Thormann tray, this narrowing is complete and the internal column diameter has contracted back to 6.00 m.

1.70 m above the uppermost Thormann tray is disposed the third collecting tray (chimney tray with 16 approximately uniformly distributed roofed chimneys, chimney height=1.50 m).

535 506 kg/h of acid water with a temperature of 65.1° C. and a pressure of −1.24 bar are withdrawn as the second side draw from the third collecting tray.

The acid water has, as already stated, the following contents:

| | | |
|---|---|---|
| 10.7677% | by wt. of | acrylic acid, |
| 6.4390% | by wt. of | acetic acid, |
| 79.5610% | by wt. of | water, |
| 0.7038% | by wt. of | formic acid, |
| 2.4712% | by wt. of | formaldehyde, |
| 0.0132% | by wt. of | acrolein, |
| 0.0082% | by wt. of | propionic acid, |
| 0.0013% | by wt. of | furfurals, |
| 0.0331% | by wt. of | allyl formate, and |
| 0.0001% | by wt. of | MEHQ, and |
| 0.0013% | by wt. of | oxygen. |

25 537 kg/h of the acid water withdrawn (65.1° C.) are recycled to the uppermost Thormann tray together with inhibitor solution 2.

329 kg/h of inhibitor solution 1 are recycled to the 19th Thormann tray (counted from the bottom) (with a temperature of 25° C.).

316 kg/h of the acid water withdrawn are sent to incineration.

310 m$^3$/h of the acid water withdrawn are recycled at a temperature of 29.1° C. to the sixth of the valve trays to be described below (counted from the bottom) (the cooling is effected by means of multistage indirect heat exchange).

194 011 kg/h of the acid water withdrawn are recycled at a temperature of 23° C. to the uppermost of the valve trays to be described below (the cooling is effected together with the aforementioned amount of acid water by means of multistage indirect heat exchange; the last cooling stage from 29.1° C. to 23° C. is effected thermally and with heat integration (liquid chemical-grade propylene is used as the coolant and evaporates at the same time; the resulting gaseous propylene is subsequently used for the configuration of the reaction gas mixture for the gas phase partial oxidation)).

1204 kg/h of the acid water withdrawn are, as already described, added to the crude acrylic acid to be purified further by crystallization.

6010 kg/h of the acid water withdrawn are fed to the extraction column for the purpose of the inventive extraction still to be performed thereafter.

2300 mm above the third collecting tray in the condensation column are mounted 11 two-flow valve trays in equidistant arrangement (tray separation=500 mm). The height of the overflow weir is from 18 to 35 mm (those of the upper trays are higher than those of the lower trays). The orifice ratio (specific bore area) is 14.8%, and the sum of the drain areas of the downcomers of two successive valve trays is ~10% of the column cross-sectional area. The valves used were VV12 valves from Stahl, Viernheim, Germany.

The pressure at the top of the column is 1.17 bar.

At the top of the column, 170 121 kg/h of residual gas leave the separating column with a temperature of 31° C. and the following contents:

| | | |
|---|---|---|
| 0.1946% | by wt of | acrylic acid, |
| 0.1246% | by wt. of | acetic acid, |
| 2.3031% | by wt. of | water, |
| 0.0062% | by wt. of | formic acid |
| 0.1212% | by wt. of | acrolein, |
| 0.0002% | by wt. of | propionic acid |
| 0.0001% | by wt. of | furfurals, |
| 0.0027% | by wt. of | allyl formate, |
| 2.3427% | by wt. of | $CO_2$, |
| 0.7609% | by wt. of | CO, |
| 0.7211% | by wt. of | propane, |
| 0.1681% | by wt. of | propylene |
| 2.7387% | by wt. of | $O_2$, and |
| 90.5158% | by wt. of | $N_2$. |

In an indirect heat exchanger, the residual gas is heated to 38° C. and then 110 880 kg/h of this residual gas are compressed to a pressure of 2.9 bar by means of a cycle gas compressor, which raises the temperature to approx. 160° C. 94 553 kg/h of the compressed cycle gas are recycled into the gas phase partial oxidation as cycle gas. 16 327 kg/h of the compressed cycle gas are fed to the first stripping column for the purpose of stripping the extract from the acid water extraction, and 59 241 kg/h of the residual gas are sent to incineration.

The extraction column for the acid water extraction comprises, as separating internals, punched structured packings fitted so as to be flush at the edge (height of a packing element: 200 mm) and made of stainless steel sheets (material 1.4571) of the Montz-Pak B1-350 type with an active total height of 10 m, which are arranged one on top of another.

The internal diameter of the extraction column over all packings is a uniform 800 mm. Their height is 14 m. The extractant used is Palatinol®A. Bottom and top vessel of the column are widened to 1100 mm in diameter in order to improve the phase separation in the bottom and reduce the entrainment of extractant in the top of the column. In addition, a bed of random plastics packings (for example polyethylene or Teflon) is introduced as a coalescence aid in the top of the column.

6010 kg/h of acid water to be extracted (temperature=65.1° C.) are fed into the extraction column below the lowermost packing via tubular distributors having appropriate passage orifices (bores of diameter 8 mm). Above the uppermost packing of the extraction column, a mixture of approx. 25 kg/h of fresh Palatinol® A) and 5987 kg/h of extractant which has been recycled from the first stripping column and has been stripped free therein beforehand (temperature=50° C.) is introduced.

The recycled extractant has the following contents:

| | | |
|---|---|---|
| ≦0.5% | by wt. of | acrylic acid, |
| ≦0.03% | by wt. of | acetic acid, |
| ≦0.02% | by wt. of | water, |
| ≦0.001% | by wt. of | formic acid, |
| ≦0.0035% | by wt. of | acrolein, |
| ≦0.0005% | by wt. of | propionic acid, |
| ≦00.001% | by wt. of | furfurals, |

-continued

| ≦0.001% by wt. of | allyl formate, |
| 0.03% by wt. of | MEHQ, |
| 0.0001% by wt. of | oxygen, and |
| ≧99.5% by wt. of | Palatinol ® A. |

The specific mass of the acid water is 967.5 kg/m³. The extractant is likewise introduced via tubular distributors having appropriate passage orifices (bores of diameter 4 mm).

The acid water forms the continuous phase and the extractant forms the phase dispersed in droplet form (droplet diameter in the range from 2 to 5 mm), which descends in the aqueous phase.

At the top of the extraction column, 4930 kg/h of raffinate (temperature ~57.6° C.) are withdrawn, which has the following contents:

| 1.7618% by wt. of | acrylic acid, |
| 4.3046% by wt. of | acetic acid, |
| 90.1197% by wt. of | water, |
| 0.6446% by wt. of | formic acid, |
| 2.8993% by wt. of | formaldehyde, and |
| 0.27% by wt. of | Palatinol ® A. |

It is sent to incineration together with residual gas to be incinerated. 7090 kg/h of extract are withdrawn from the bottom of the extraction column, which has the following contents (temperature ~64.5° C.)

| 8.1556% by wt. of | acrylic acid, |
| 2.4838% by wt. of | acetic acid, |
| 4.7901% by wt. of | water, |
| 0.1490% by wt. of | formic acid, |
| 0.0788% by wt. of | formaldehyde, |
| 0.0140% by wt. of | acrolein, |
| 0.0073% by wt. of | propionic acid, |
| 0.0014% by wt. of | furfurals, |
| 0.0282% by wt. of | allyl formate, and |
| 0.0192% by wt. of | MEHQ, |
| 84.2726% by wt. of | Palatinol ® A. |

The entirety of the extract is conducted to the top of the first stripping column. Beforehand, the extract is heated to 95° C. by indirect heat exchange in a plate heat exchanger. The heat carrier used is 5987 kg/h of bottoms liquid withdrawn at the first stripping column. The first stripping column comprises, as separating internals, 5 dual-flow trays and 15 Thormann trays. Just like the extraction column, the first stripping column is insulated thermally from the environment. The internal diameter of the first stripping column over all trays is a uniform 1.5 m.

Its height is 14.5 m. The lowermost 5 trays are configured as dual-flow trays and are arranged equidistantly (500 mm) in the first stripping column. Their orifice ratio is a uniform 18%. The hole diameter of the dual-flow trays is a uniform 14 mm (hole arrangement corresponding to strict triangular pitch). Above the uppermost dual-flow tray are disposed 15 single-flow Thormann trays which are arranged equidistantly (separation 500 mm). The Thormann trays are configured such that a mutually opposite flow direction of the liquid is obtained in each case in channels successive in crossflow direction via the arrangement of the motive slots in the hoods of the Thormann trays. The orifice ratio (gas passage area based on the cross section) is 14%.

Above the last tray is also disposed a bed (height 400 mm, Pall rings made of metal, 25×25) as a droplet trap.

Below the lowermost dual-flow tray, 13 000 m³ (STP)/h of compressed residual gas (pressure ~2.9 bar, temperature ~160° C.) are conducted into the first stripping column, where it ascends in countercurrent to the extract descending in the stripping column.

At the top of the first stripping column, 17 424 kg/h of first laden gas are conducted out (temperature=82.2° C.) and fed to the second stripping column. The temperature in the bottom of the first stripping column is approx. 155° C. 49 311 kg/h of bottoms liquid are withdrawn continuously from the bottom of the first stripping column. 5987 kg/h of the bottoms liquid withdrawn from the first stripping column are cooled to 50° C. by two-stage indirect heat exchange (the first stage in a plate heat exchanger with thermal integration against extract), and recycled to the top of the extraction column. 43 324 kg/h of bottoms liquid withdrawn from the first stripping column are heated to 160° C. in an external force-circulation tube bundle flash evaporator and recycled into the bottom of the first stripping column.

Comparative Example

The procedure is like the example, except the acid water extracted in the example is not extracted but rather incinerated as in the prior art.

The extraction column and the first stripping column are dispensed with. To strip the bottoms liquid withdrawn from the condensation column, the corresponding amount of compressed residual gas is used. The stream of crude acrylic acid withdrawn via the first side draw is 87 307 kg/h and comprises 96.863% by weight of acrylic acid. The amount of glacial acrylic acid to be fed to the storage tank is 16 994 kg/h. Its purity is 99.736% by weight of acrylic acid.

Example 2

498 g of acid water which had not been admixed with inhibitor and had a temperature of 50° C. were introduced into a jacketed stirred vessel stirred with a two-level, three-blade stirrer (thermostated with water) with an internal volume of 1.3 l at 50° C., and had the following contents:

| 2.19% by wt. of | formaldehyde, |
| 82.00% by wt. of | water, |
| 4.01% by wt. of | acetic acid, |
| 11.09% by wt. of | acrylic acid, |
| 0.69% by wt. of | formic acid, and |
| 0.01% by wt. of | diacrylic acid. |

499 g of dimethyl phthalate which were likewise at 50° C. were then added with stirring. At a constant temperature of 50° C., the resulting mixture was stirred at a speed of 250 revolutions/min over 10 min. After the stirrer had been switched off, the mixture was left alone at 50° C., and phase separation occurred within a short time. The mass of the organic phase was 565 g; the mass of the aqueous phase was 432 g. Gas chromatography analysis of the aqueous phase showed that it still comprised 20.26 g of acrylic acid and 13.0 g of acetic acid.

Example 3

To extract acrylic acid from acid water, an extraction column made of glass was used. The acid water which had not been admixed with inhibitor had the following contents:

| | |
|---|---|
| 2.36% by wt. of | formaldehyde, |
| 83.12% by wt. of | water, |
| 3.98% by wt. of | acetic acid, |
| 9.70% by wt. of | acrylic acid, |
| 0.68% by wt. of. | formic acid, and |
| 0.01% by wt. of | diacrylic acid. |

The extraction column was thermostatable (with water at 60° C.) through a jacket. The separating internals present in the extraction column were structured stainless steel sheet metal packings (type 1.4404 stainless steel, punched packings from Montz of the B1-350 type). The internal diameter of the extraction column in the packed part was 40 mm. 10 kg/h of the aqueous solution (temperature=60° C.) were conducted into the bottom of the column. At the top of the extraction column, 10 kg/h of diethyl phthalate were fed in (temperature=60° C.) in countercurrent as the dispersed phase (droplet size: from 4 to 5 mm). The aqueous raffinate conducted out at the top of the column still comprised 0.8% by weight of acrylic acid and 2.9% by weight of acetic acid. It was thus possible to deplete the content of acrylic acid in the acid water (based on the original content by weight) by 93.3% by weight and that of acetic acid by 41% by weight. 0.2% by weight of diethyl phthalate were dissolved in the raffinate.

Example 4

The procedure was as in example 3. As the extractant and dispersed phase, 27.5 kg/h of dimethyl phthalate (T=60° C.) were introduced at the top of the extraction column (droplet size: from 4 to 5 mm). The acid water, of which a flow rate of 27.5 kg/h had likewise been fed with a temperature of 60° C. into the bottom of the column as a continuous phase, had the following contents:

| | |
|---|---|
| 2.77% by wt. of | formaldehyde, |
| 82.82% by wt. of | water, |
| 4.02% by wt. of | acetic acid, |
| 9.53% by wt. of | acrylic acid, |
| 0.63% by wt. of | formic, and |
| 0.05% by wt. of | diacrylic acid. |

The aqueous raffinate descending at the top of the extraction column still comprised 0.2% by weight of acrylic acid and 2.4% by weight of acetic acid. It was thus possible to deplete the content of acrylic acid in the acid water (based on the original content by weight) by 98.3% by weight and that of acetic acid by 51.5% by weight. 0.9% by weight of dimethyl phthalate was dissolved in the raffinate.

Example 5

The procedure is as in example 1. In addition to the reflux liquid (acid water), 1000 kg/h of water (additional absorbent) are conducted into the condensation column together with it and with the same temperature. The furfural content of the crude acrylic acid conducted out of the condensation column as the first side draw from the second collecting tray, as a result, falls from 0.1642% by weight (value in example 1) to 0.1225% by weight.

Example 6

The procedure is as in example 1. In addition to the reflux liquid (acid water), 5000 kg/h of water (additional absorbent) are conducted into the condensation column together with it and with the same temperature. The furfural content of the crude acrylic acid conducted out of the condensation column as the first side draw from the second collecting tray, as a result, falls from 0.1642% by weight (value in example 1) to 0.1125% by weight.

The invention claimed is:

1. A process for preparing acrylic acid, comprising passing a product gas mixture comprising acrylic acid, steam and secondary components which is obtained by heterogeneously catalyzed gas phase partial oxidation of at least one $C_3$ precursor of acrylic acid with molecular oxygen over solid-state catalysts at elevated temperature, into a condensation column equipped with separating internals, allowed to ascend into itself within the condensation column and thus fractionally condensed, and crude acrylic acid comprising a reduced total amount of water and secondary components is conducted as the target product out of the condensation column via a first side draw disposed above the feed point of the product gas mixture into the condensation column, acid water still comprising acrylic acid and secondary components is conducted out of the condensation column via a second liquid phase draw disposed above the first side draw, and a portion of said acid water withdrawn is recycled as such and/or after cooling thereof as reflux liquid into the condensation column, a residual gas mixture comprising secondary components having lower boiling points than water is conducted out of the condensation column at the top of the condensation column, and a bottoms liquid still comprising acrylic acid and conversion products and secondary components having higher boiling points than acrylic acid is conducted out of the condensation column from the bottom space of the condensation column, wherein at least from a portion of acid water not recycled into the condensation column acrylic acid present in it is taken up from the acid water into an organic solvent by extraction with the organic solvent to form an organic extract comprising acrylic acid, then acrylic acid is removed from the organic extract by stripping with a first stripping gas and the resulting acrylic acid-laden first stripping gas is recycled into the condensation column and/or the acrylic acid present in the first laden stripping gas is taken up into the aqueous solution of a metal hydroxide, or is used as a second stripping gas in order to strip acrylic acid out of bottoms liquid conducted out of the condensation column, and the resulting acrylic acid-laden second stripping gas is recycled into the condensation column and/or the acrylic acid present in the second stripping gas is taken up into the aqueous solution of a metal hydroxide.

2. The process according to claim 1, wherein the $C_3$ precursor is propylene or acrolein or a mixture of propylene and acrolein.

3. The process according to claim 1 or 2, wherein acrylic acid present at least in 25% by weight of acid water not recycled into the condensation column is taken up from the acid water into an organic solvent by extraction with the organic solvent to form an organic extract comprising acrylic acid.

4. The process according to any of claims 1 or 2 wherein the extraction of the acrylic acid from the acid water is performed in an extraction column which comprises structured packings and/or sieve trays as separating internals.

5. The process according to claim 4, wherein the organic solvent is introduced at the top of the extraction column and the acid water in the bottom region of the extraction column, and the organic solvent ascends as a dispersed phase in the continuous acid water phase, or wherein the acid water is introduced at the top of the extraction column and the organic solvent in the bottom region of the extraction column, and the organic solvent ascends as a dispersed phase in the continuous acid water phase.

6. The process according to any of claims 1 or 2, wherein the organic solvent comprises at least one ester of an aliphatic or aromatic monocarboxylic acid comprising from 5 to 20 carbon atoms and an alcohol having from 1 to 8 carbon atoms.

7. The process according to any of claims 1 or 2, wherein the organic solvent comprises at least one diester of an aliphatic or aromatic dicarboxylic acid comprising from 5 to 20 carbon atoms and an alcohol having from 1 to 8 carbon atoms.

8. The process according to any of claims 1 or 2 wherein the organic solvent is at least one solvent selected from the group consisting of dimethyl phthalate, diethyl phthalate, dimethyl isophthalate, diethyl isophthalate, dimethyl terephthalate and/or diethyl terephthalate.

9. The process according to any of claims 1 or 2, wherein the boiling point of the organic solvent at atmospheric pressure is $\geq 200°$ C.

10. The process according to any of claims 1 or 2, wherein the stripping of the bottoms liquid conducted out of the condensation column is performed in a stripping column provided with separating internals, and the temperature in the bottom of the stripping column is from 150 to 190° C.

11. The process according to any of claims 1 or 2, wherein the acrylic acid-laden second stripping gas is subjected to a countercurrent rectification before it is recycled into the condensation column laden with acrylic acid and/or the acrylic acid present therein is taken up into the aqueous solution of a metal hydroxide.

12. The process according to any of claims 1 or 2, wherein the first stripping gas used is air, $N_2$, $CO_2$ and/or steam.

13. The process according to any of claims 1 or 2, wherein the first stripping gas used is residual gas mixture.

14. The process according to any of claims 1 or 2, wherein the crude acrylic acid is purified further by crystallization.

15. The process according to claim 14, wherein a portion of the acid water not recycled into the condensation column is added to the crude acrylic acid before the crystallizative further purification.

16. The process according to claim 14 wherein the crystallizative further purification of the crude acrylic acid or the mixture thereof with acid water is effected by suspension crystallization.

17. The process according to claim 16, wherein a wash column is used additionally to separate mother liquor remaining in the suspension crystallization and suspension crystals formed.

18. The process according to claim 14 which is followed by a process for free-radical polymerization in which molten acrylic acid crystals and/or the metal salt thereof is polymerized.

19. The process according to any of claim 1 or 2, which is followed by a process for free-radical polymerization in which acrylic acid taken up from laden first and/or second stripping gas into the aqueous solution of a metal hydroxide is polymerized.

20. The process according to any of claims 1 or 2, wherein a portion of the residual gas mixture is recycled as cycle gas into the gas phase partial oxidation.

21. The process according to any of claims 1 or 2, wherein the organic solvent has a mass density which, under the conditions of the extraction, differs from that of water by $\geq 25$ kg/m$^3$.

22. The process according to any of claims 1 or 2, wherein the aqueous solution of a metal hydroxide comprises NaOH, KOH, $Ca(OH)_2$ and/or $Mg(OH)_2$ in dissolved form.

23. The process according to any of claims 1 or 2, wherein a liquid absorbent whose boiling point $T_s$ at a pressure of 1 atm is greater than or equal to the boiling point $T_w$ of water at a pressure of 1 atm is fed to the condensation column via a feed point disposed between its first side draw and its second side draw.

24. The process according to claim 1, further comprising reducing a temperature of said product gas mixture by direct and/or indirect cooling prior to introduction into said condensation column.

25. The process according to claim 1, further comprising subjecting said crude acrylic acid conducted from said first side draw to one or more further thermal separation process for the purpose of its further purification.

* * * * *